US007567913B2

(12) United States Patent
Bennett et al.

(10) Patent No.: US 7,567,913 B2
(45) Date of Patent: Jul. 28, 2009

(54) METHOD AND SYSTEM FOR ORDERING A LABORATORY TEST FOR A PATIENT AND OBTAINING RESULTS THEREOF

(75) Inventors: Richard Joseph Bennett, Lakewood, CO (US); Albert A. Tate, Bethel Park, PA (US); David Andrew Rapperport, Coral Springs, FL (US); Ryan Michael Eastman, Austin, TX (US); Randall Scott DeBold, St. Louis, MO (US)

(73) Assignee: Quest Diagnostics Inc., San Juan Capistrano, CA (US)

( * ) Notice: Subject to any disclaimer, the term of this patent is extended or adjusted under 35 U.S.C. 154(b) by 1795 days.

(21) Appl. No.: 09/784,889

(22) Filed: Feb. 16, 2001

(65) Prior Publication Data
US 2002/0161606 A1 Oct. 31, 2002

(51) Int. Cl.
*G06F 19/00* (2006.01)
(52) U.S. Cl. ............................... 705/3; 705/2
(58) Field of Classification Search ................ 705/2, 705/3
See application file for complete search history.

(56) References Cited

U.S. PATENT DOCUMENTS

| 5,715,314 | A | | 2/1998 | Payne et al. ................ 705/78 |
| 6,018,713 | A | * | 1/2000 | Coli et al. ................... 705/2 |
| 2001/0051880 | A1 | * | 12/2001 | Schurenberg et al. ......... 705/3 |
| 2002/0007284 | A1 | * | 1/2002 | Schurenberg et al. ......... 705/2 |
| 2002/0116224 | A1 | * | 8/2002 | Hengerer et al. ............. 705/3 |

* cited by examiner

*Primary Examiner*—Gerald J. O'Connor
*Assistant Examiner*—Lena Najarian
(74) *Attorney, Agent, or Firm*—Jon Gordon; Frommer Lawrence & Haug LLP

(57) ABSTRACT

A method is provided for receiving an order for a laboratory test of a biological specimen for a patient utilizing a computer network including a client computer and a central computer. The method includes facilitating a connection between the client computer and the central computer. A laboratory test request is received at the central computer from the client computer. Patient, billing, and diagnosis information corresponding to the requested laboratory test is also received at the central computer from the client computer. Information is transmitted from the central computer to the client computer for generating a test requisition and a label for use with the biological specimen.

8 Claims, 22 Drawing Sheets

| Standing Orders for Patient: | | Testing, Olga | | |
|---|---|---|---|---|
| Standing Order Codes: max codes allowed 15. | File Standing Orders Reminder: Only order those tests which are medically necessary for the diagnosis and treatment of the patient | | | |
| | Optional Expiration Date: | | | |
| 418 | | | | |
| | | | | |
| | | | | |

Description:

Search by: ○ Code  ● Description  [Search]

| Order Code | Description |
|---|---|

[Close]

| Order Code | Component | Question | Answer |
|---|---|---|---|
| 7943 | CREATININE CLEARANCE | HEIGHT FEET | |
| | | HEIGHT INCHES | |
| | | WEIGHT POUNDS | |
| | | URINE VOLUME | |
| | | COLLECTION TIME | |

<<Back  Continue>>

Please Note:
A signed Advance Beneficiary Notice (ABN) is required for this requisition and must accompany the sample

ABN Queries

1. Will the patient sign an ABN form?   ○ Yes  ○ No
2. Is the patient here to sign an ABN?   ○ Yes  ○ No
3. Are there any other medically appropriate diagnosis codes in the patient's chart for this date of service?   ○ Yes  ○ No Submit ABN Rules Documentation © Copyright 2001, Quest Diagnostics Incorporated. All rights reserved Doe, Jane M
Client : 97502840
Req : 0030486

| Edit Order | Save Order |

Order Verification for Patient: Testing,Olga

Client 97502840 - TEST CLIENT (HQ)
UPIN D09876 - Test,Doc

Patient Information:

SSN 201201201                    ID 1234567890 12345
Last Name Testing
First Name Olga                  MI
DOB 09/11/1976                   Sex F
Address any                      City LODI
State AL                         Zip 07644
Phone 2019999999
Billing Type Insurance

Responsible Party:

Relationship Spouse              SSN 201201201
Last Name Testing
First Name Olga                  MI
DOB 09/11/1976                   Sex F
Address any                      City LODI
State AL                         Zip 07644
Phone 2019999999
Group #
Ins ID 123456789A
Physician ID Test,Doc
Insurance Carrier MCR - MEDICARE

Tests Ordered:

| Code | Description |
| --- | --- |
| 7943 | # CREATININE CLEARANCE |
| 418 | DIGOXIN |

Requisition Level Diagnoses:

Query Results — Page 1 of 2

| Req ID | Date | Name | DOB | Age | Sex | Value |
|---|---|---|---|---|---|---|
| 0001772 | 09/07/2000 | DUGAN, CAROLE L | 01/03/1957 | 43 | F | 140 |
| 0001879 | 09/10/2000 | DUGAN, CAROLE L | 01/03/1957 | 43 | F | 145 |
| 0001881 | 09/11/2000 | DUGAN, CAROLE L | 01/03/1957 | 43 | F | TNP |
| 0001959 | 09/18/2000 | DUGAN, CAROLE L | 01/03/1957 | 43 | F | 140 |
| 0001774 | 09/07/2000 | LABORDE, LESLIE | 08/04/1977 | 23 | F | 140 |
| 0001775 | 09/07/2000 | LABORDE, LESLIE | 08/04/1977 | 23 | F | 145 |
| 0001776 | 09/07/2000 | LABORDE, LESLIE | 08/04/1977 | 23 | F | 147 - H |
| 0001778 | 09/07/2000 | LABORDE, LESLIE | 08/04/1977 | 23 | F | 134 - L |
| 0001779 | 09/07/2000 | LABORDE, LESLIE | 08/04/1977 | 23 | F | 145 |
| 0001781 | 09/07/2000 | LABORDE, LESLIE | 08/04/1977 | 23 | F | 137 |
| 0001782 | 09/07/2000 | LABORDE, LESLIE | 08/04/1977 | 23 | F | 136 |
| 0001784 | 09/07/2000 | LABORDE, LESLIE | 08/04/1977 | 23 | F | 139 |
| 0001785 | 09/07/2000 | LABORDE, LESLIE | 08/04/1977 | 23 | F | 140 |
| 0001786 | 09/07/2000 | LABORDE, LESLIE | 08/04/1977 | 23 | F | 147 - H |
| 0001787 | 09/07/2000 | LABORDE, LESLIE | 08/04/1977 | 23 | F | 136 |
| 0001788 | 09/07/2000 | LABORDE, LESLIE | 08/04/1977 | 23 | F | 150 - H |
| 0001789 | 09/07/2000 | LABORDE, LESLIE | 08/04/1977 | 23 | F | 138 |
| 0001790 | 09/07/2000 | LABORDE, LESLIE | 08/04/1977 | 23 | F | 135 |
| 0001791 | 09/07/2000 | LABORDE, LESLIE | 08/04/1977 | 23 | F | 148 - H |
| 0001792 | 09/07/2000 | LABORDE, LESLIE | 08/04/1977 | 23 | F | 142 |

[Quit] [New Query] [Next]

© Copyright 2001, Quest Diagnostics Incorporated. All rights reserved.

FIG. 8F

Cumulative Reporting

| | |
|---|---|
| Client | TEST CLIENT (HQ) |
| SSN | |
| Number of Reports to go back | 2 |

[Quit] [Query]

© Copyright 2001, Quest Diagnostics Incorporated. All rights reserved.

METHOD AND SYSTEM FOR ORDERING A LABORATORY TEST FOR A PATIENT AND OBTAINING RESULTS THEREOF

TECHNICAL FIELD

The present invention relates, in general, to a computer method and system for ordering a test and obtaining results thereof. More particularly, this invention relates to a method and system for ordering laboratory tests for a patient and obtaining test results over the Internet.

BACKGROUND OF THE INVENTION

In the field of laboratory testing, medical professionals request laboratory tests on behalf of their patients as an important part of the delivery of medical services. A biological sample (e.g., blood, urine, culture, etc.) is taken from the patient by the medical professional. That biological sample is often transported to an independent laboratory, which is requested to conduct a specified test on the biological sample. The results of the test are then communicated by the laboratory to the medical professional. In such a process, steps should be taken to maintain patient confidentiality, handle the biological samples efficiently, and report test results accurately. Over the years, attempts have been made to streamline the process, to reduce costs, and to minimize the paperwork associated with laboratory testing of biological samples.

The Internet includes a vast number of computers and computer networks that are interconnected through communications links. The interconnected computers exchange information using various services, such as electronic mail, Gopher, and the World Wide Web (WWW). The WWW service allows a server computer system (i.e., Web server or Web site) to send graphical Web pages of information to a remote client computer. The remote client computer can then display the Web pages. Each resource (e.g., computer or Web page) of the WWW is uniquely identifiable by a Uniform Resource Locator (URL). To view a specific Web page, a client computer specifies the URL for that Web page in a request (e.g., a Hyper-Text Transfer Protocol (HTTP) request). The request is forwarded to the Web server that supports that Web page. When that Web server receives the request, it sends that Web page to the client computer. When the client computer receives that Web page, it typically displays the Web page using a browser. A browser is a special-purpose application program that affects the requesting of Web pages and the displaying of Web pages.

Web pages are typically defined using Hyper-Text Markup Language (HTML). HTML provides a standard set of tags that define how a Web page is to be displayed. When a user indicates to the browser to display a Web page, the browser sends a request to the server computer system to transfer to the client computer an HTML document that defines the Web page. When the requested HTML document is received by the client computer, the browser displays the Web page as defined by the HTML document. The HTML document contains various tags that control the displaying of text, graphics, controls, and other features. The HTML document may contain URLs of other Web pages available on that server computer system or other server computer systems.

The World Wide Web is especially conducive to conducting electronic commerce. Many Web servers have been developed through which vendors can advertise and sell products. The products can include items (e.g., music) that are delivered electronically to the purchaser over the Internet and items (e.g., books) that are delivered through conventional distribution channels (e.g., a common carrier). A server computer system may provide an electronic version of a catalog that lists the items that are available. A user, who is a potential purchaser, may browse through the catalog using a browser and select various items that are to be purchased. When the user has selected the items to be purchased, the server computer system then prompts the user for information to complete the ordering of the items. This purchaser-specific order information may include the purchaser's name, the purchaser's credit card number, and a shipping address for the order. The server computer system then typically confirms the order by sending a confirming Web page to the client computer system and schedules shipment of the items.

SUMMARY OF THE INVENTION

The present invention is embodied in a method of receiving an order for a laboratory test of a biological specimen for a patient utilizing a computer network including a client computer and a central computer. The method includes facilitating a connection between the client computer and the central computer. A laboratory test request is received at the central computer from the client computer. Patient, billing, and diagnosis information corresponding to the requested laboratory test is also received at the central computer from the client computer. Information is transmitted from the central computer to the client computer for generating a test requisition and a label for use with the biological specimen.

According to another aspect of this invention, a method is also provided for providing results of a laboratory test of a biological specimen using a computer network including a client computer and a central computer laboratory test results are received at the central computer. A request for laboratory test results is received at the central computer from the client computer. An identification of a patient or group of patients is also received at the central computer from the client computer. The laboratory test results are then transmitted to the client computer.

It is understood that the foregoing general description and the following detailed description are exemplary, but are not restrictive, of the invention.

BRIEF DESCRIPTION OF THE DRAWING

The invention is best understood from the following detailed description when read in connection with the accompanying drawing. Included in the drawing are the following figures:

FIGS. 8A through 8F are embodiments of screen snapshots of various pages or documents provided by the method shown in FIG. 5 for obtaining results of tests ordered for a patient in the computer network of FIG. 1;

Figures 10, 11:
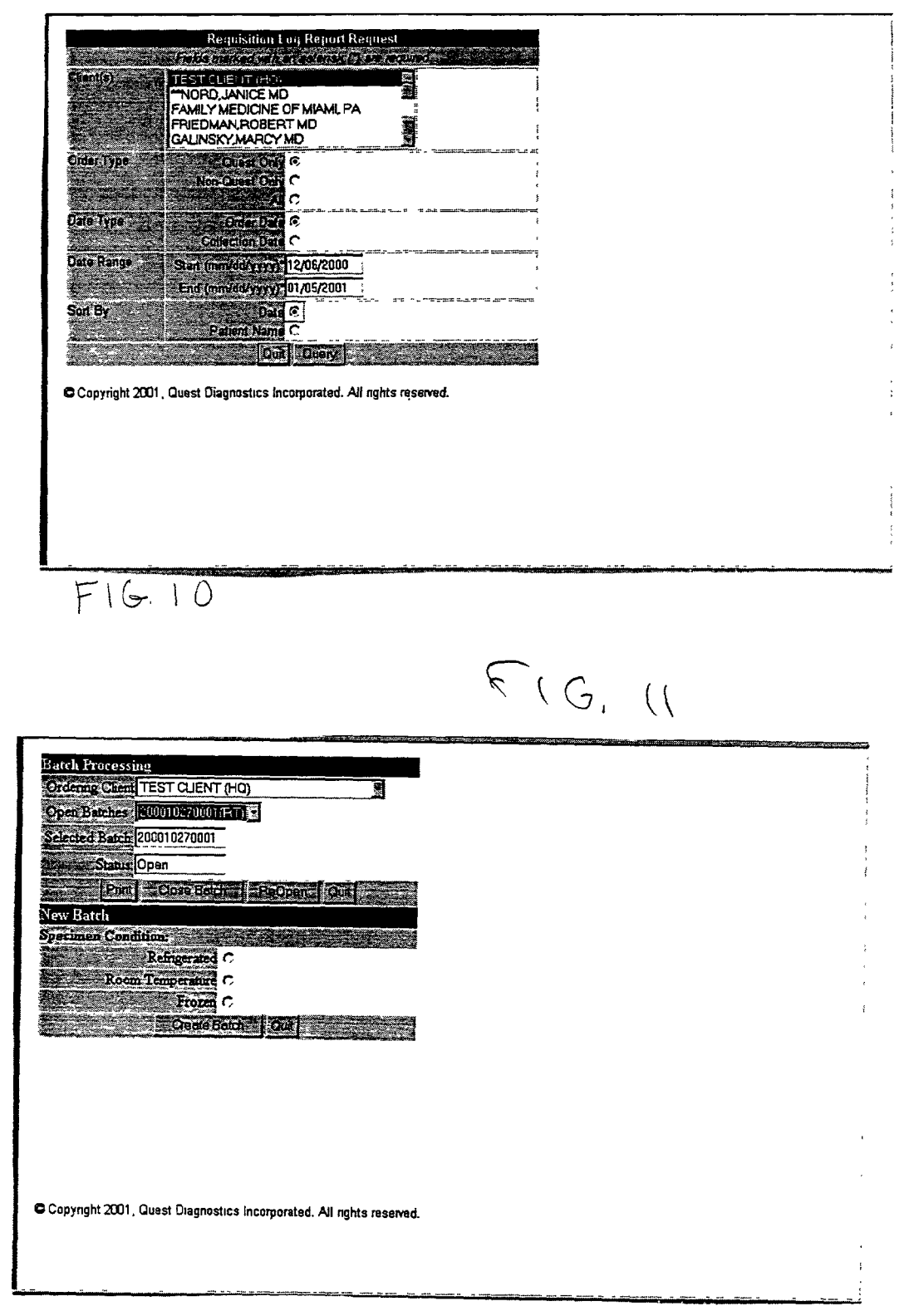

FIG. 10 is an embodiment of a screen snapshot of a requisition-log-report-request page for providing a log of all requisitions filed by a client in the computer network of FIG. 1; and FIG. 11 is an embodiment of a screen snapshot of a manifest report to view the orders for a batch of tests ordered by a client in the computer network of FIG. 1.

FIG. 12 is an embodiment of a screen snapshot of a generic test ordering screen.

DETAILED DESCRIPTION OF THE INVENTION

Exemplary embodiments of this invention will now be described with reference to the figures. It should be appreciated that this invention is not limited to the embodiments selected for illustration in the figures. It should also be appreciated that variations and modifications to the exemplary embodiments can be made without departing from the spirit or scope of this invention.

Generally, this invention provides a Web-based test ordering and results reporting system that enables physician and hospital clients of a separate laboratory to access patient laboratory test results via the Internet in a secure and reliable way. In other words, the exemplary embodiment of the invention makes it possible to provide an Internet laboratory ordering application that facilitates electronic ordering of laboratory tests by physicians and other medical professionals. The exemplary embodiment can be used by the physicians (or other medical professionals) as well as by organized physician groups to provide an interface with the laboratory. Alternatively, the system according to this invention can be adapted for use with patient service centers of the laboratory.

Figure 1:
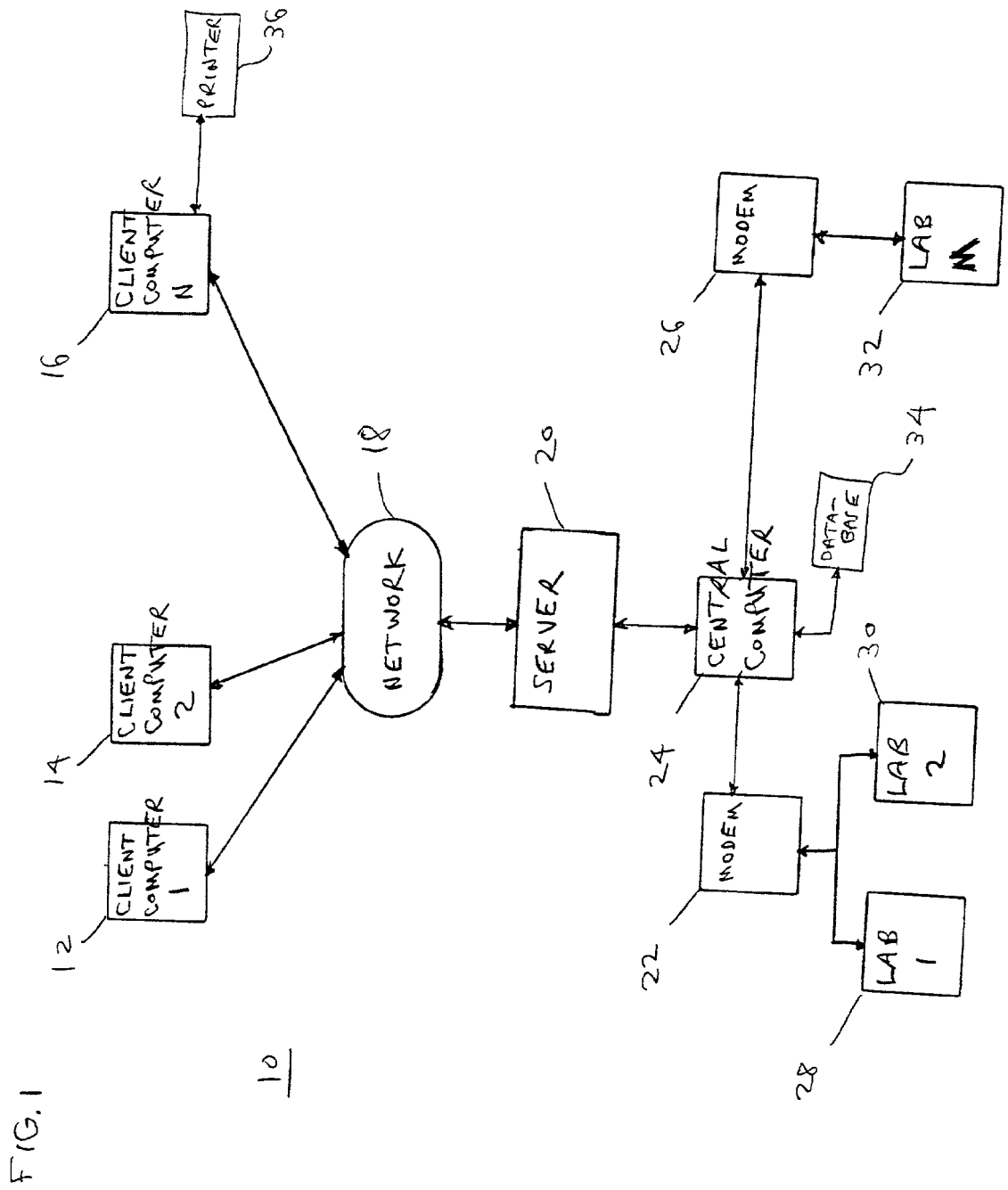
FIG. 1 is a block diagram of an embodiment of a computer network system in accordance with the present invention.
Figures 7A, 7B:
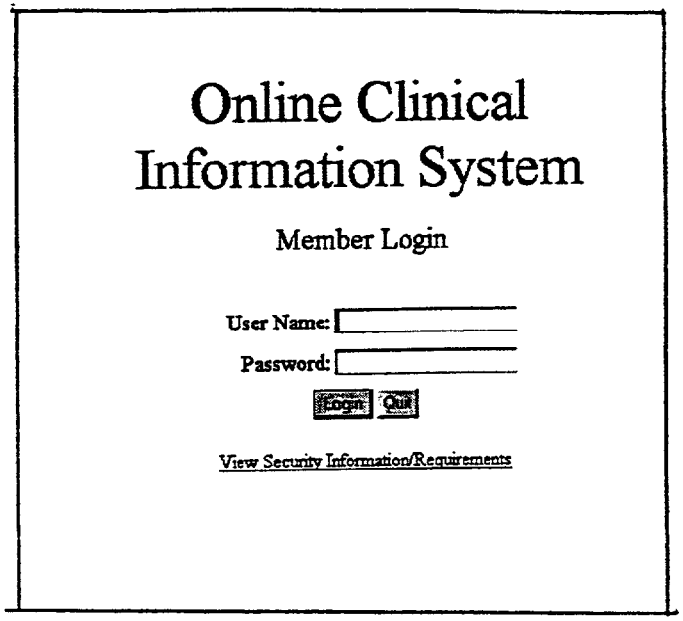
FIGS. 7A through 7N are embodiments of screen snapshots of various pages or documents provided by the method shown in FIG. 3 for ordering a test for a patient in the computer network of FIG. 1.
Figures 7C, 7D:
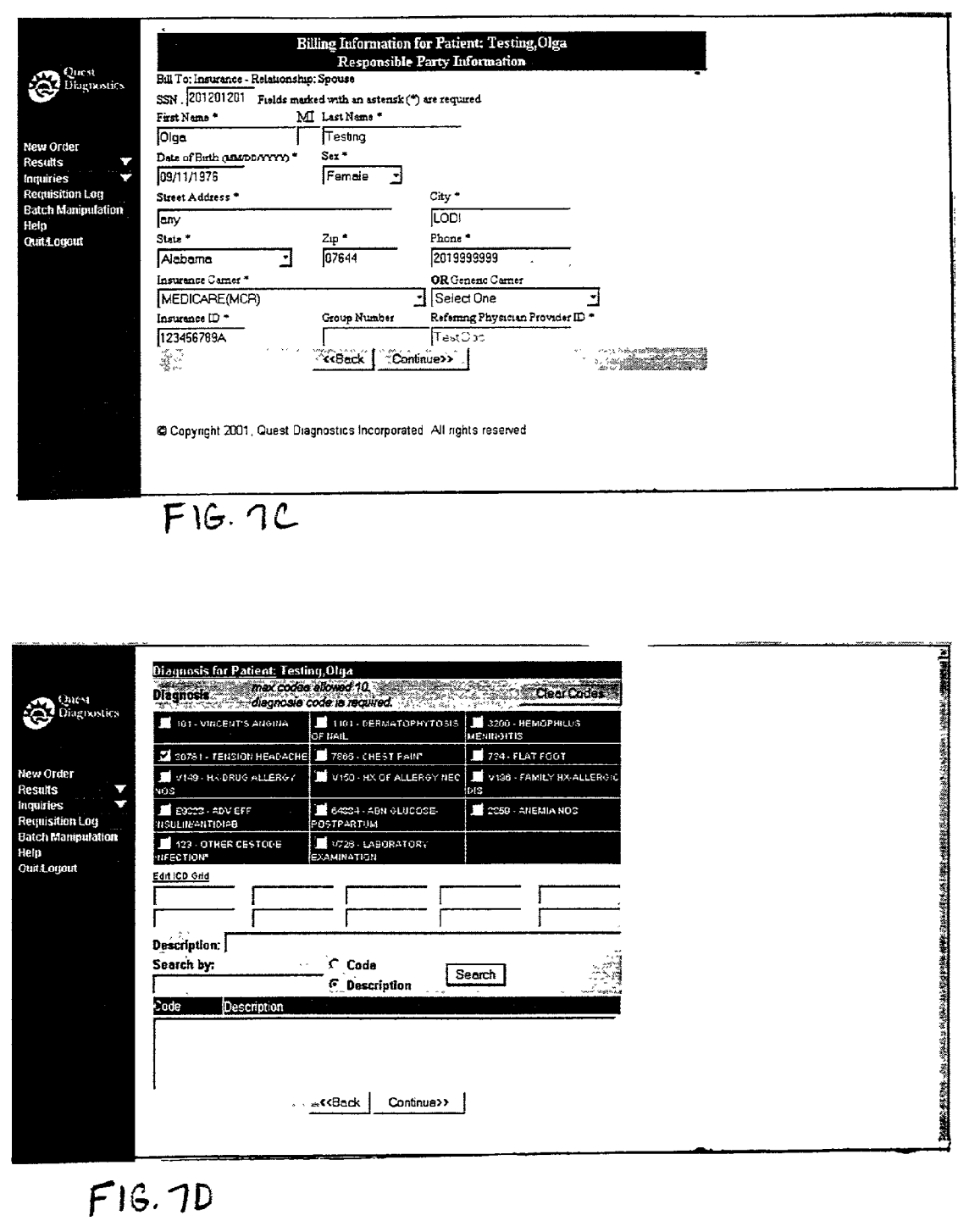

Referring generally to the figures, an exemplary method of ordering a laboratory test of a biological specimen for a patient using a computer network such as the computer network system 10 is shown in FIG. 1. A patient-identification query such as the query illustrated in FIG. 7B is transmitted to a client computer 1, 2, N, thereby soliciting information about the patient for whom the test is being ordered. A billing-information query such as the query illustrated in FIG. 7C is also transferred to the client computer 1, 2, N, thereby soliciting information about a party responsible for payment of the test being ordered for the identified patient. A patient diagnosis query such as the query illustrated in FIG. 7D is also transmitted to the client computer 1, 2, N, thereby soliciting at least one diagnosis for the identified patient. A test-order query such as the query illustrated in FIG. 7E can also be transmitted to the client computer 1, 2, N, thereby soliciting a request for at least one test for the biological specimen of the identified patient.

Exemplary details of an embodiment of the invention will now be described. With reference to FIG. 1, a computer network system, generally designated as 10, includes at least one client computer from which a doctor or other medical professional desiring to order a laboratory test for a patient can communicate with a central computer 24. As shown, client computers 1, 2, N designated respectively as 12, 14, 16, are each interconnected by way of network 18 and server 20 to central computer 24. Network 18 may be the Internet.

As will be described in greater detail, a user of a client computer 12, 14, 16 can order a laboratory test by communicating with the central computer 24. Central computer 24 coordinates and manages each order received from a client computer. Central computer 24 can be connected for communication with several laboratories that may perform a test being ordered by a client computer. As shown, central computer 24 communicates with laboratory 1 and laboratory 2, designated respectively as 28 and 30, by way of modem 22. Central computer 24 also communicates with laboratory M, designated as 32, through the network or by way of modem 26 as shown in FIG. 1. Data is stored in database 34.

In the embodiment shown in FIG. 1, central computer 24 communicates through the network with the laboratories.

As will be explained in detail, computer network system 10 provides an on-line ordering system. Application programs residing in the central computer permit electronic ordering of laboratory tests by a physician or a hospital for a patient. Application programs residing in the central computer permit electronic reporting of laboratory test results to the physician or hospital or elsewhere, as desired. The system also provides administrative functions such as verifying that a specific test order is eligible for payment by an insurance plan or informing the physician or hospital client that a specific test order is not payable by the insurance plan based on the diagnosis codes identified for the patient. Customized diagnosis code grids and test order code grids may be built by a physician or hospital, for example, to facilitate ordering of tests.

Figure 2:
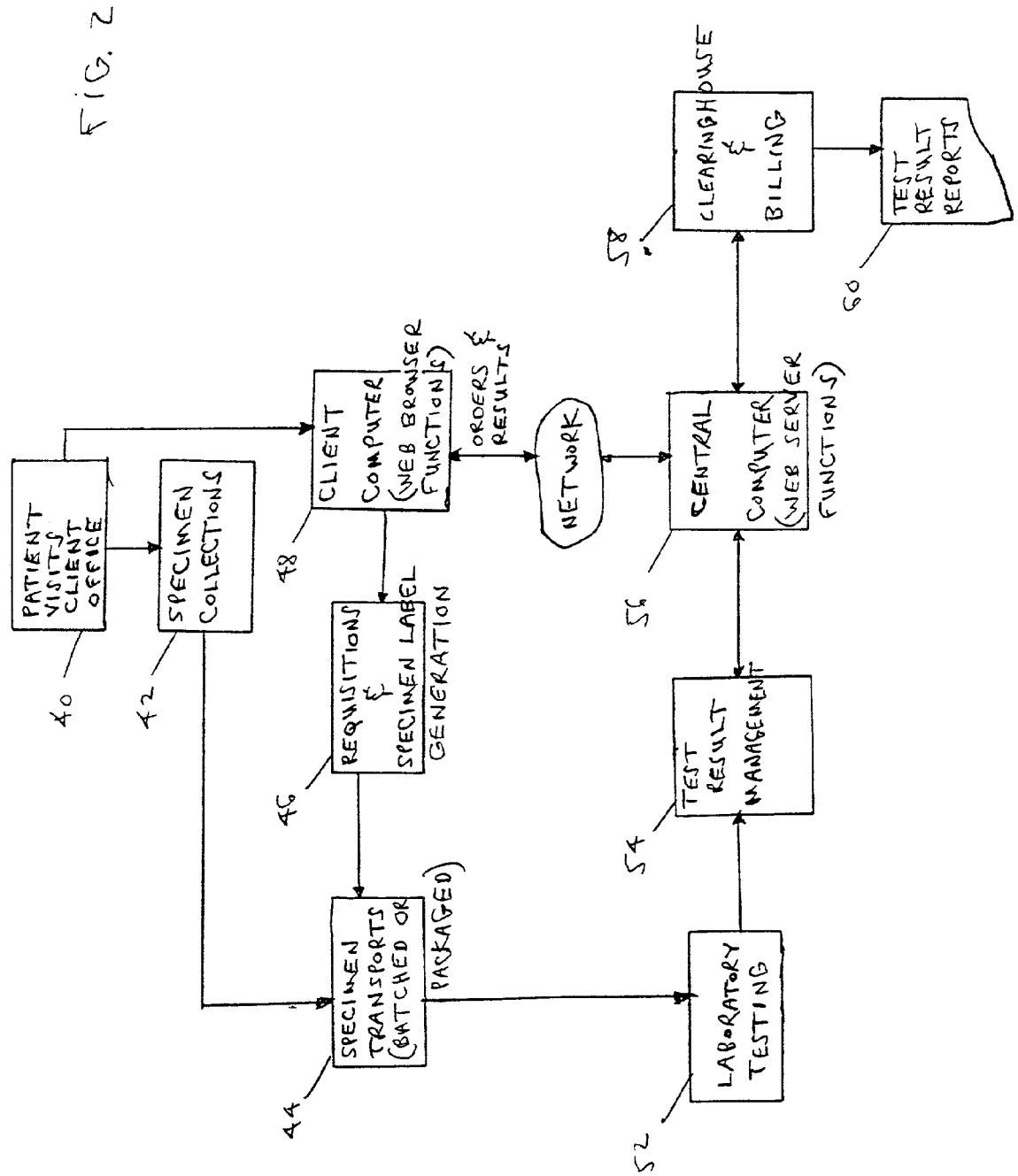
FIG. 2 is a flowchart diagram illustrating an embodiment of the operation of ordering a test for a patient and obtaining the test results in the computer network system of FIG. 1.

FIG. 2 depicts a functional logic flow diagram of the method performed by the exemplary system. As shown, a patient visits a client office in step 40. The client office may be a patient service center (PSC), a physician's office or a hospital, for example. Specimens are collected in step 42 for the patient. The specimens may include blood and urine, for example. The client, using the Web browser function in the client computer, sends a specific URL (universal resource locator) to the Web server of the central computer. The Web server fetches a log-in page from the database and sends it to the client's computer. After the client logs in with the correct user name and user password, the Web server sends an ordering document URL to the client's Web browser. The client fills in the test order and sends a test order URL to the Web server. It will thus be appreciated to those skilled in the art that steps 48 and 56 are a series of steps, whereby the client computer communicates with the central computer to order a test to ascertain the results of a test and to handle administrative functions associated with the test order, such as billing and customizing of pages showing diagnosis codes and test order codes. Exemplary details of the steps included in steps 48 and 56, shown in FIG. 2, will be explained later.

Figure 7E:
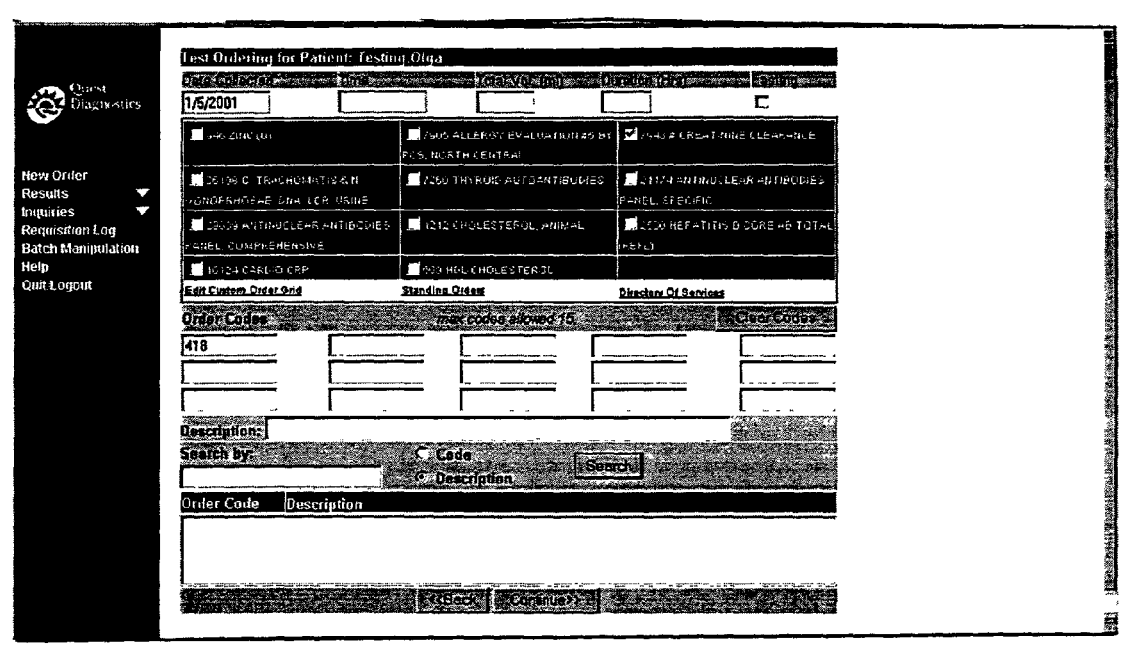
Figure 7G:
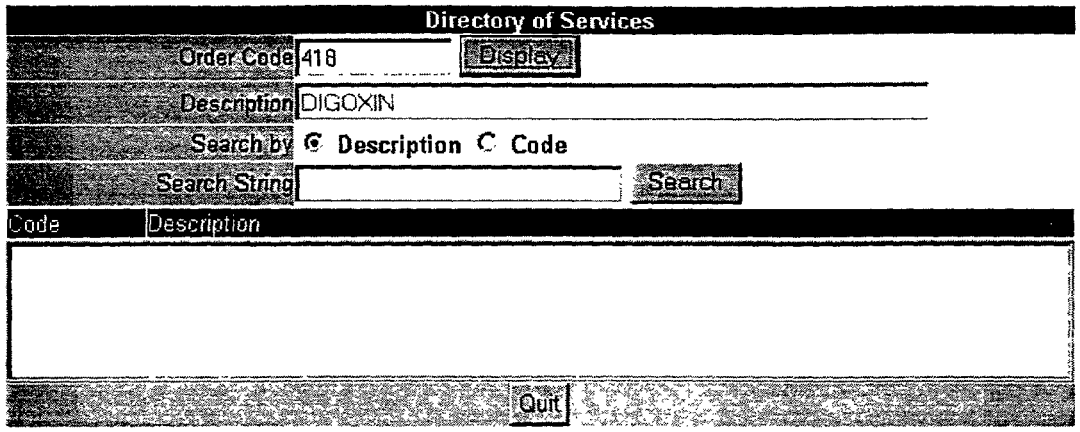
Figure 7H:
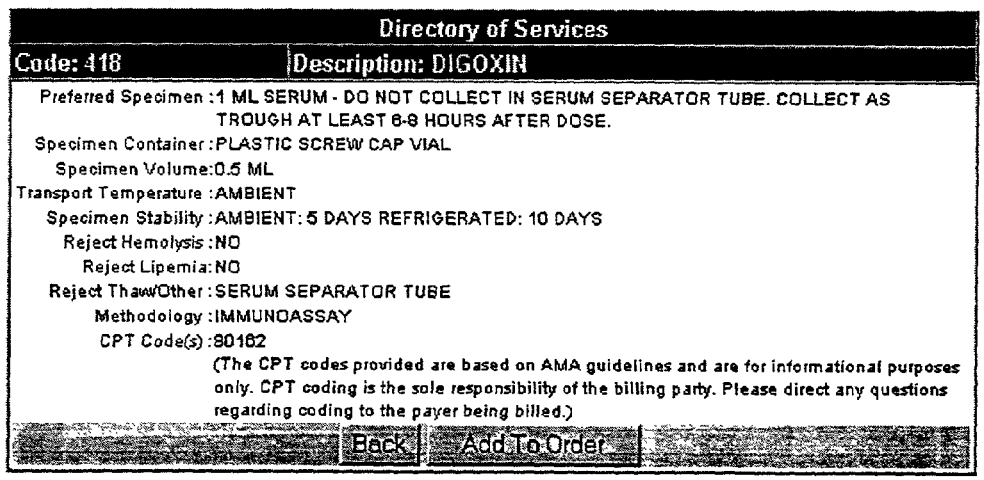
Figure 7L:
Figure 7N:
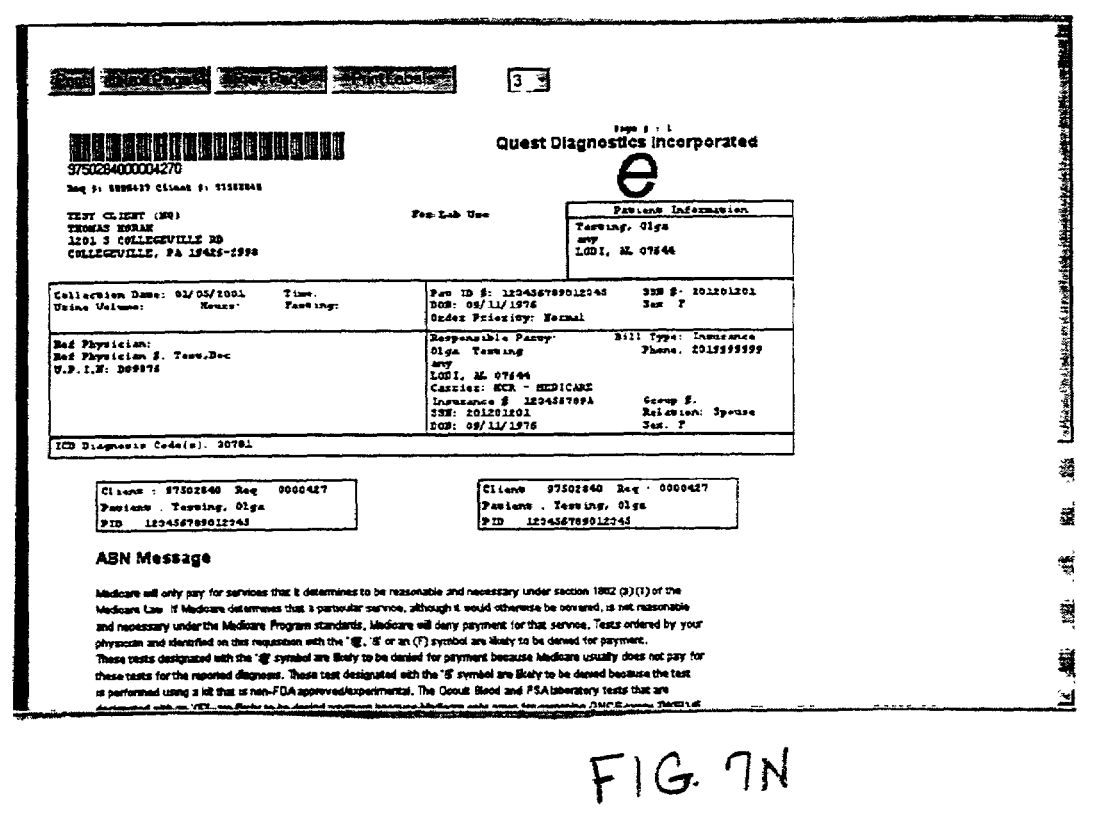

Upon successful communications to order a test by the client computer, a requisition for the test (as illustrated in FIG. 7N) and specimen labels (as illustrated in FIG. 7L) are generated in step 46. The labels may include information correlating the specimen to the patient and the test requisition. For example, the labels include the patient's name, a client identification number, a requisition number, and a machine-readable code (e.g., a barcode). For example, one of the labels shown in FIG. 7L includes the patient name "Doe, Jane M."; client number "97502840"; requisition number "0030486", and a barcode.

The requisitions and specimen labels may be generated by print commands from the client computer to a printer (for example printer 36, shown in FIG. 1) connected to the client computer. The printed label is placed on the specimen collected from the patient to identify the specimen. The specimen is accompanied by the printed requisition and transported in step 44 to a laboratory for testing. As will be explained, the specimen may be transported as a single package or batched together with other specimens based on the specimen transport type (frozen, room temperature, refrigerated, etc). Batching provides an advantage to the client in that many specimens from different patients may be placed in a common container for transport. The lab courier may then transport the specimens to the performing laboratory.

The performing laboratory receives the specimen and performs testing in step 52. The results of the test are sent to the central computer, either manually or by instrument merge, in test result management step 54. If instrument merge is used, the test results are measured by laboratory instruments and patient results are then merged into the patient's file and transmitted to the laboratory system. The central computer (or a computer at the performing laboratory) may interpret the test result and provide an alert or an abnormal flag for the attention of the doctor in the event that the test report includes test results that do not fall within a predetermined "normal" range. As will be explained, the central computer performs functions of a clearinghouse, shown as step 58, ensuring that a test ordered from a client is paid by a responsible party and that someone assumes responsibility of payment for the test.

Test results are released by the central computer to the client computer in step 60. Test results may be provided by electronic transmission over the network, when requested by the client computer. As explained later, demographic results may also be provided to the client computer. Other methods for providing test results to the client in step 60 include sending results by mail, courier or facsimile transmission.

Figure 3:
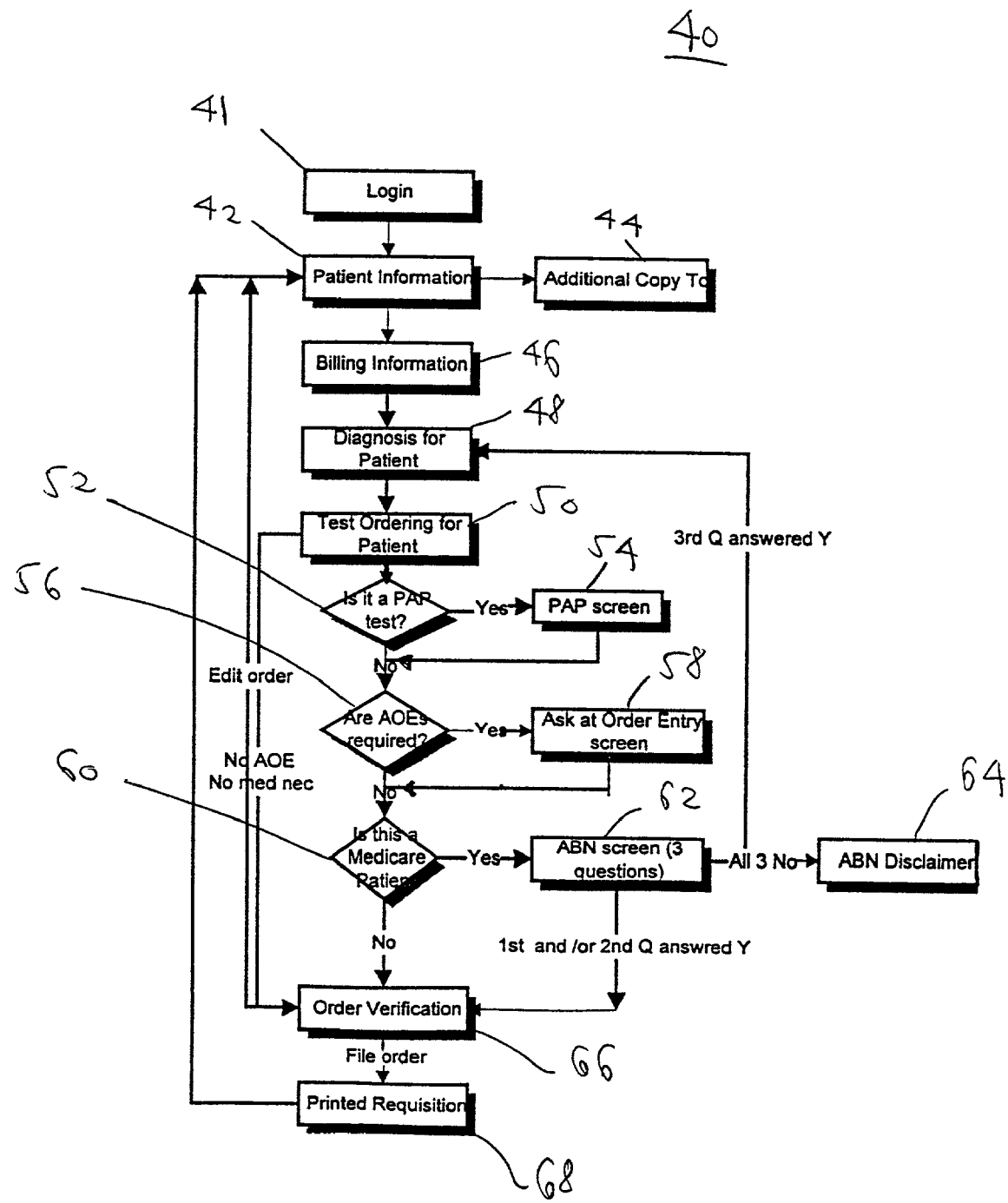
FIG. 3 is a flowchart diagram illustrating in greater detail an embodiment of a method of ordering a test for a patient in the computer network of FIG. 1.

In an exemplary embodiment of the invention, a method for ordering a test on a specimen taken from a patient is shown in FIG. 3. The method, generally designated as 40, exchanges information between a client computer and a central computer on a communications network. A test order is begun when the Web browser of the client computer requests a log-in page from Web server of the central computer in step 41. After receiving the log-in page, the client provides a user name and a password to the Web server. Details of the log-in page are provided later.

Assuming that the user name and password are recognized by the server, an introductory page is displayed. When the user clicks on New Order, a patient information page is displayed. The patient information page is sent to the client browser in step 42. The client browser presents the patient information page on the screen or display of the client computer. The client enters the requested information regarding the patient. Details of the patient information page are provided later. A hard copy of the patient information page (or any other page) may be provided to the client or another party by clicking on a Hypertext presented on the page in step 44.

Although the pages can be provided to the client in a variety of orders, a billing information page may be presented next to the client Web browser in step 46. The client enters the requested information including the identification of the responsible party and the name of the insurance program for billing of the test. Details of the billing information page are provided later.

A diagnosis-for-patient page is presented to the Web browser in step 48. It will be appreciated that when ordering a test for a patient, the client enters a diagnosis code (ICD) identifying a diagnosis for the patient. One or more ICDs may be entered for the patient. Details of the diagnosis-for-patient-page are provided later.

After entering an ICD for the patient, the Web browser is presented with a test-ordering-for-patient page in step 50. The client may now enter order codes for the tests being ordered. Details of the test-ordering-for-patient page presented on the screen of the client computer are provided later.

In one embodiment of the invention, the diagnosis-for-patient page and the test-ordering-for-patient page may be customized by the client. In this manner, codes most commonly used by a particular client for identifying diagnoses of its patients and tests ordered for its patients that are medically necessary for treatment of the patients may be presented on the client's computer screen every time the client computer communicates with the central computer. For example, a gynecologist is typically interested in a set of test orders for specific diagnoses of his or her patient that is different from the set of test orders and diagnoses made by an orthopedist or an internist for his or her patients. By allowing each client to customize the code grids, the system is personalized, user friendly and flexible.

Further flexibility in the exemplary ordering method of the invention is provided by a decision box 52. If a PAP test is being ordered by the client, for example, decision box 52 branches to step 54 and presents a PAP page on the screen of the computer. Although a PAP test is discussed here for purposes of illustration, other particular tests can be identified to trigger a separate test screen.

If a PAP (or other predetermined) test is not being ordered, the method branches to decision box 56 and determines whether additional information is required for the specific test being ordered. If ask-at-order-entry (AOE) questions are required for the test being ordered, the method branches to step 58 and presents an AOE page on the display. The AOE page prompts the client for answers to a specific set of questions required for the test (for example: height and weight of the patient). After the client answers the questions (if applicable), the ordering method enters decision box 60.

In the embodiment shown in FIG. 3, decision box 60 determines, based on the identified patient and the identified insurance plan, whether the patient is a Medicare patient (for example). If the patient is a Medicare patient, the method branches to step 62 and provides an advance beneficiary notice (ABN) page on the display screen of the client computer. The exemplary ABN page includes three questions, as shown in Table 1. The questions may be answered "yes" or "no". If the client answers all three questions with "no", the method provides a disclaimer notice in step 64. The disclaimer notice is shown in Table 2. If the client answers the third question with "yes", the method branches to step 48 and presents the diagnosis-for-patient page on the display and allows the client to enter any other medically appropriate diagnosis for the patient. If the client answers at least one of the first and second questions with "yes", the method branches to step 66.

It will be appreciated that the invention in another embodiment may provide ABN alerts to the client for patients that have an insurance plan other than Medicare. By providing a look-up table in database 34 (FIG. 1), correlating patient's test order codes with diagnosis codes, the method may determine if the test being ordered is medically necessary and payable under the insurance plan.

After completing the patient-information page, the billing-information page, the diagnosis-for-patient page, the test-ordering-for-patient page, any required AOEs (if applicable), and the ABN page (if applicable), the client is prompted in step 66 to verify and file the order. If the client notices mistakes or omissions, the client is permitted to again access any one of the previously filled-in pages by looping back to step 46. After the order is verified and filed, the exemplary-method may cause a printer at the client computer to print a requisition in step 68. The method provides an order-verification-for-patient page on the display in step 66 and a requisition page on the display in step 68. Both pages are described in detail later.

If appropriate, an ABN is printed on the requisition with a signature box. The patient, if available, signs the ABN, thereby indicating that the patient is responsible for payment of the test order. An example of an ABN page that can be printed on the requisition is shown in Table 3.

TABLE 1

Advance Beneficiary Notice (ABN) Alert.

Please Note:
A signed Advance Beneficiary Notice (ABN) is required for this requisition and must accompany the sample.

| | |
|---|---|
| Will the patient sign an ABN form? | Y/N |
| Is the patient here to sign an ABN? | Y/N |
| Are there any other medically appropriate diagnosis codes in the patient's chart for this date of service? | Y/N |

TABLE 2

Disclaimer Notice

Based on the diagnosis code(s) entered for this order, the services: TEST NAME; TEST NAME are not considered medically necessary by Medicare in accordance with the Local Medical Review Policies in effect where the specimen will be tested. Because an Advance Beneficiary Notice (ABN) has not been signed by the patient, the Administrator will not be able to bill the patient if it is not reimbursed by Medicare for the services provided to your patient. Therefore, if you continue to order non-medically necessary tests, as determined by Medicare, the Administrator may be forced to make other billing arrangements with your office.

Note:
TEST NAME(s) is inserted dynamically

TABLE 3

ABN Printed on the Requisition

Advance Beneficiary Notice
Medicare will only pay for services that it determines to be reasonable and necessary under section 1862 (a) (1) of the Medicare Law. If Medicare determines that a particular service, although it would otherwise be covered, is not reasonable and necessary under the Medicare Program standards, Medicare will deny payment for that service. Tests ordered by your physician and identified on this requisition with the "@", "&" or an "(F)" symbol are likely to be denied for payment. Those tests designated with the "@" symbol are likely to be denied for payment because Medicare usually does not pay for these tests for the reported diagnosis. Those tests designated with the "&" symbol are likely to be denied because the test is performed using a kit that is non-FDA approved/experimental. The Occult Blood and PSA laboratory tests that are designated with an "(F)" are likely to be denied payment because Medicare only pays for screening ONCE every TWELVE months. By signing the "Advance Beneficiary Notice" on this requisition, you are confirming your agreement to assume financial responsibility for the payment of these tests.
Medicare Beneficiary Signature:_____

Figure 4:
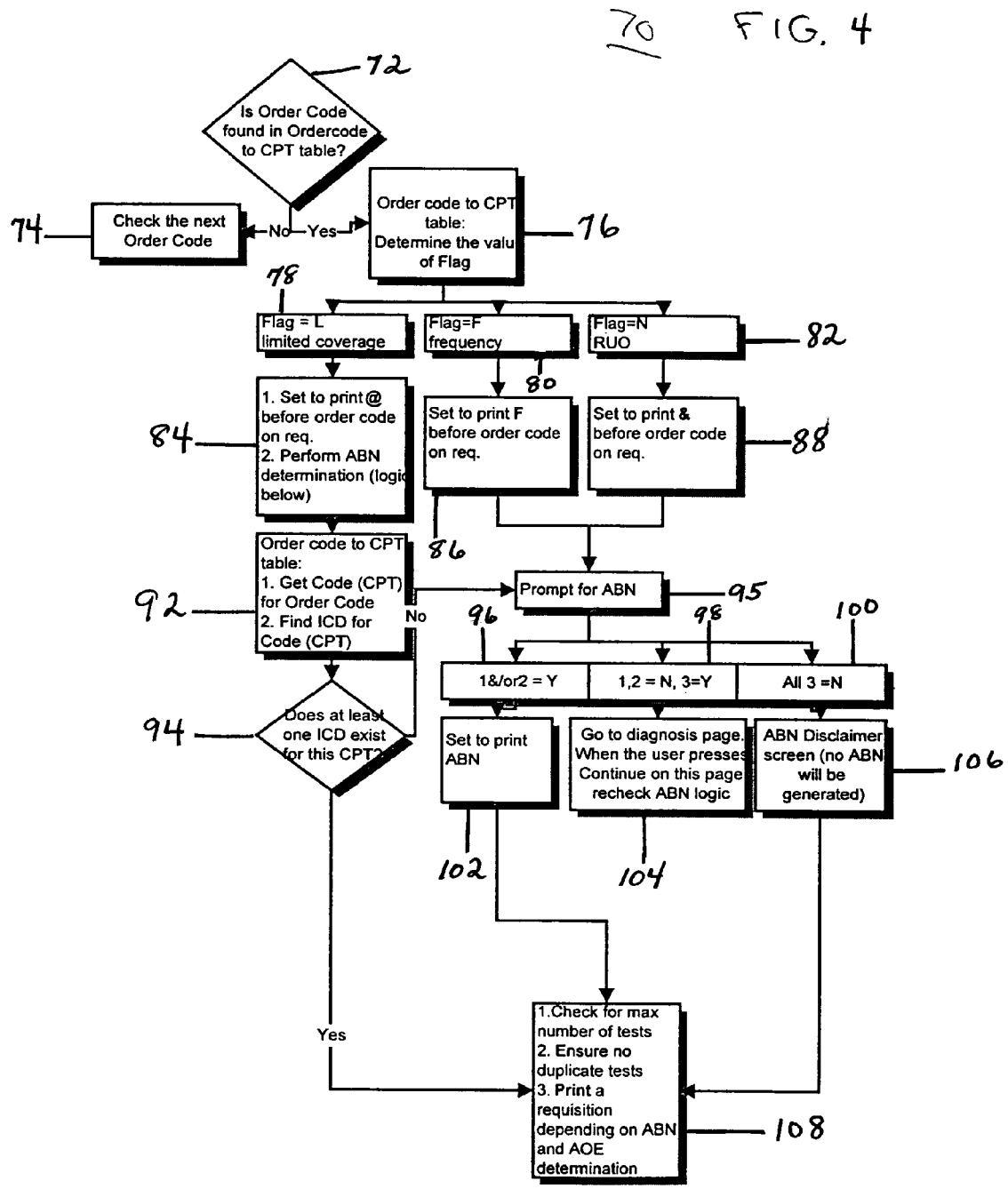
FIG. 4 is a flowchart diagram illustrating an embodiment of a method for determining whether a test being ordered for a patient in the computer network of FIG. 1 is payable by an insurance plan and alerting a client through an advance beneficiary notice (ABN), if the test being ordered is not payable by the insurance plan.

Referring next to FIG. 4, there is shown a method, generally designated 70, for determining the medical necessity category of each test and providing the ABN page on the display screen of the client computer, in response to the payment status. The method is entered at decision box 72, after the client selects at least one order code and has selected at least one diagnosis code (ICD). The method determines whether the order code is found in an Order Code-CPT table stored in database 34. If the order code is not found, the method branches to step 74 and checks the next order code selected by the client. If the order code is found in the table, the method branches to step 76 and determines a value flag associated with the order code. In the embodiment shown in FIG. 4, three value flags are shown, as an example, in determination steps 78, 80 and 82, respectively.

If the flag value is "L", or limited coverage, step 84 is entered and a symbol "@" is set to be printed on the requisition. If the flag value is "F", or based on a frequency (for example, one test per year), step 86 is entered and a symbol "F" is set to be printed on the requisition. If the flag value is "N", or research-use-only (RUO), step 88 is entered and a symbol "&" is set to be printed on the requisition.

In the embodiment of FIG. 4, the system may include a regionally based medical necessity limited coverage policy (MLCP). Medicare policies are state specific. Whether a test belongs to a limited coverage category or whether an ICD diagnosis code is paid for by Medicare is determined by the state.

It will be appreciated that in the embodiment of FIG. 4, as an example, the method uses at least one ICD code payable for each CPT in the Order Code-CPT table. The method does not allow entering a test order without first entering an ICD code for the patient. After entering an ICD code for a test order, step 90 searches the Order Code-CPT table to find the ICD codes associated with the CPT code being ordered. Step 94 determines whether at least one ICD code exists for the CPT code entered by the client for the test order.

If an ICD code exists for the CPT code, step 94 branches to step 108 and (1) checks for the maximum number of tests allowed per requisition, (2) ensures no test orders are duplicated, and (3) prints the requisition (dependent on the ABN and AOE).

ratory, and the client. Finally, step 108 is entered via step 106 (or step 102) and, as previously described, the requisition is printed based on the ABN and AOE determinations.

The flow logic for the exemplary method 70 is summarized in Table 4, showing the symbols, ABN, ABN alert and disclaimer provided to the client based on the three value flags used, as an example.

TABLE 4

ABN Logic for a Test Order

| Flag in Order CPT | ICD is Payable | Display Prompt - ABN Alert | Questions in Display Prompt - user response | | | Display Prompt - Disclaimer | Print ABN | Symbol Printed and Sent |
|---|---|---|---|---|---|---|---|---|
| | | | 1 | 2 | 3 | | | |
| L | N | Y | N | N | N | Y | Y | @ |
| L | N | Y | N | N | Y | Enter ICD code(s) and perform med. nec. checking again | Only if new code is not payable | @ |
| L | N | Y | N | Y | N/a | N | Y | @ |
| L | N | Y | Y | N/a | N/a | N | Y | @ |
| L | Y | N | N/a | N/a | N/a | N | N | @ |
| N | N/a | Y | N | N | N | Y | Y | & |
| N | N/a | Y | N | N | Y | Enter ICD code(s) and perform med. nec. checking again | Y | & |
| N | N/a | Y | N | Y | N/a | N | Y | & |
| N | N/a | Y | Y | N/a | N/a | N | Y | & |
| F | N/a | Y | N | N | N/a | Y | Y | F |
| F | N/a | Y | N | N | Y | Enter ICD code(s) and perform med. nec. checking again | Y | F |
| F | N/a | Y | N | Y | N/a | Y | Y | F |
| F | N/a | Y | Y | N/a | N/a | N | Y | F |

If an ICD code does not exist for the CPT code, step 94 branches to step 95 and an ABN prompt alert is displayed on the display screen of the client computer. An example of the ABN prompt alert was shown in Table 1. The ABN prompt alert is also provided on the display screen of the client computer via steps 86 or 88, as shown.

As described previously, the ABN prompt alert provides three questions to be answered by the client. If in step 96 the client answers question 1 and/or question 2 with a "yes", step 102 is entered and an ABN is set to be printed on the requisition. An example of an ABN was shown in Table 3, which includes a signature space for the patient.

If in step 98 the client answers question 1 and 2 with a "no" and question 3 with a "yes", step 104 is entered. The method fetches and displays the diagnosis page on the screen of the client computer, so that the client may enter another ICD code. When the client (user) finishes entering another ICD code and clicks on the "continue" button, step 104 rechecks the ABN logic by looping back to step 72.

If in step 100 the client answers all three questions with a "no", step 106 is entered and a disclaimer notice is displayed on the screen. An example of a disclaimer notice was shown in Table 2. The disclaimer notice alerts the client that the test being ordered is not considered medically necessary by the insurer (Medicare, for example) based on the ICD code entered. The client is also alerted that other billing arrangements may be necessary between the administrator, or labo- The exemplary system may provide search capability on many pages, such as test-ordering-for-patent, diagnosis-for-patient and directory-of-services. The search may be performed without page refreshing. In this manner, the information does not need to be re-entered once the page returns the search results. It is a direct database access with field level updates without the Web page refreshing.

A patient search may return all patients under the default client, all patients for the entire laboratory, or all clients. In this manner, the Patient Service Center module prioritizes patients, first under the same ordering physician, and then under all clients with the same patient name.

Figure 5:
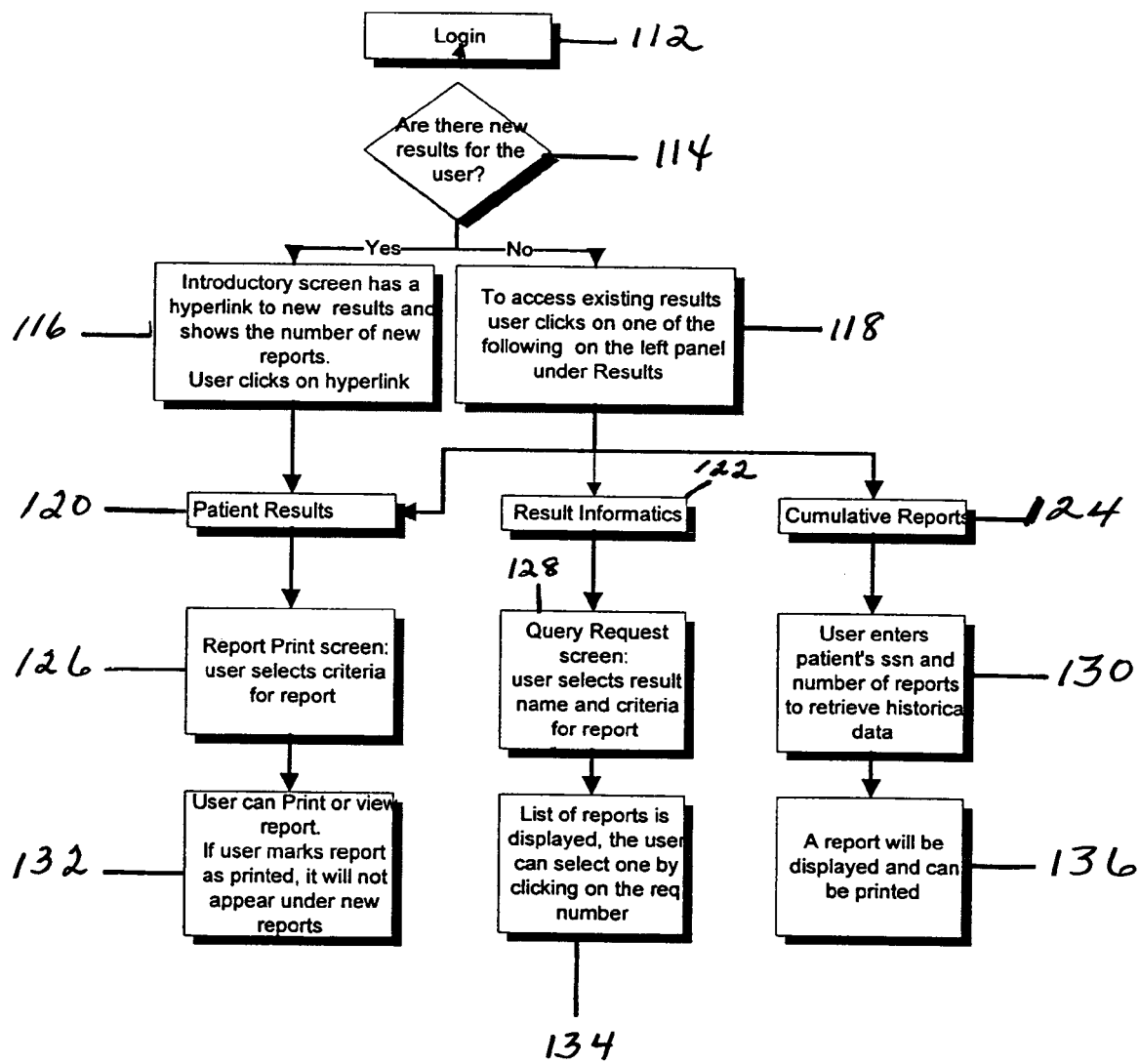
FIG. 5 is a flowchart diagram illustrating an embodiment of a method for obtaining results of tests ordered for a patient in the computer network of FIG. 1.
Figures 8A, 8B:
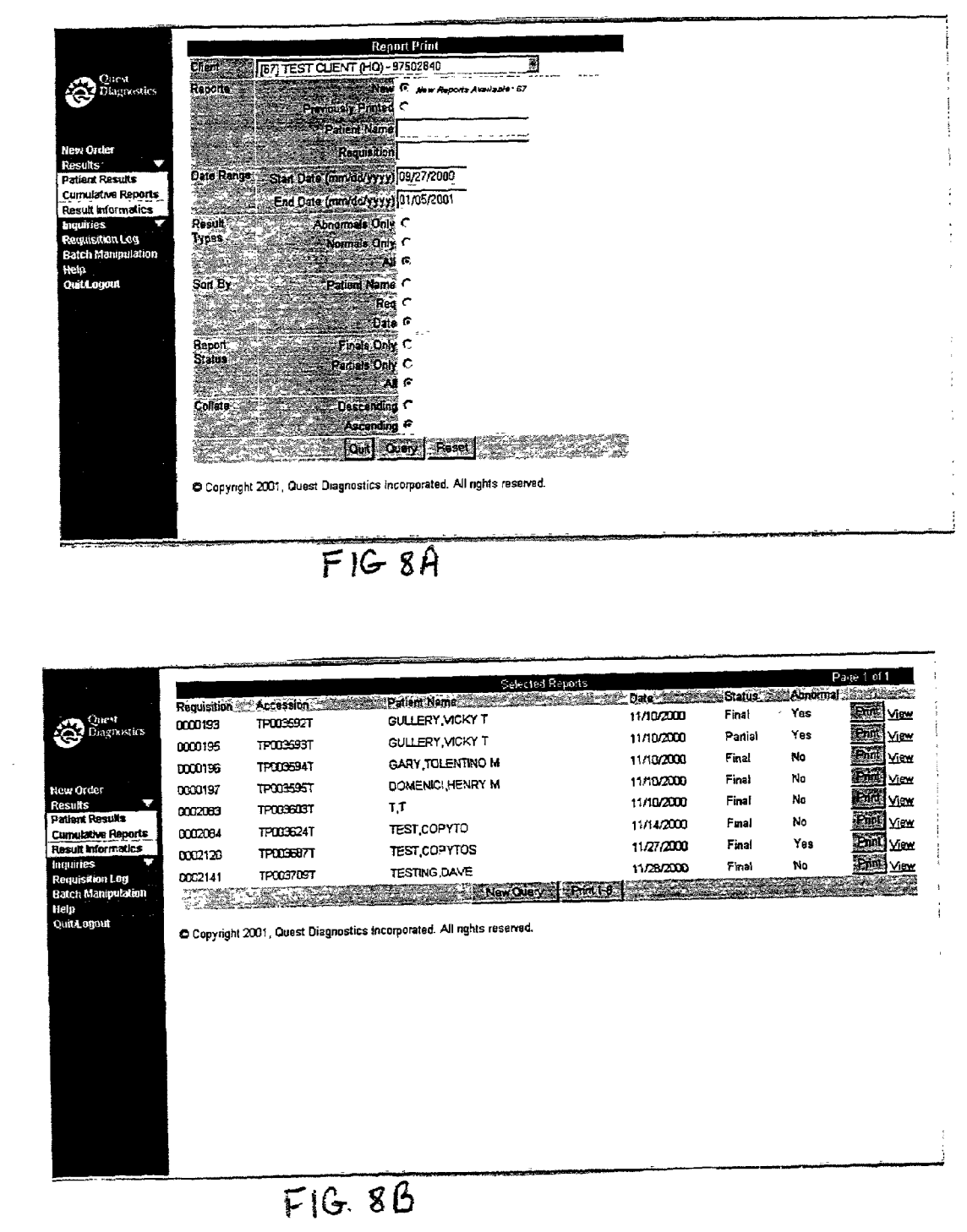

Referring next to FIG. 5, there is shown a method, generally designated 110, for obtaining test results from the computer network system. As shown, the method may be entered after log-in step 112. After successful log-in, decision box 114 determines whether there exists new test results for the client. Either step 116 or step 118 is then entered, depending on whether new results exist or do not exist. The client (user) may access existing results by clicking on Results on the menu bar presented on the left side of the screen (FIG. 8A, for example). After clicking on Results, the client may select Patient Results (step 120), Result Informatics (step 122), or Cumulative Reports (step 124). A hyperlink may also be provided on the screen in step 116, if new reports are available for printing or viewing. By clicking on the hyperlink, the client may also enter Patient Results (step 120).

Figures 8C, 8D:
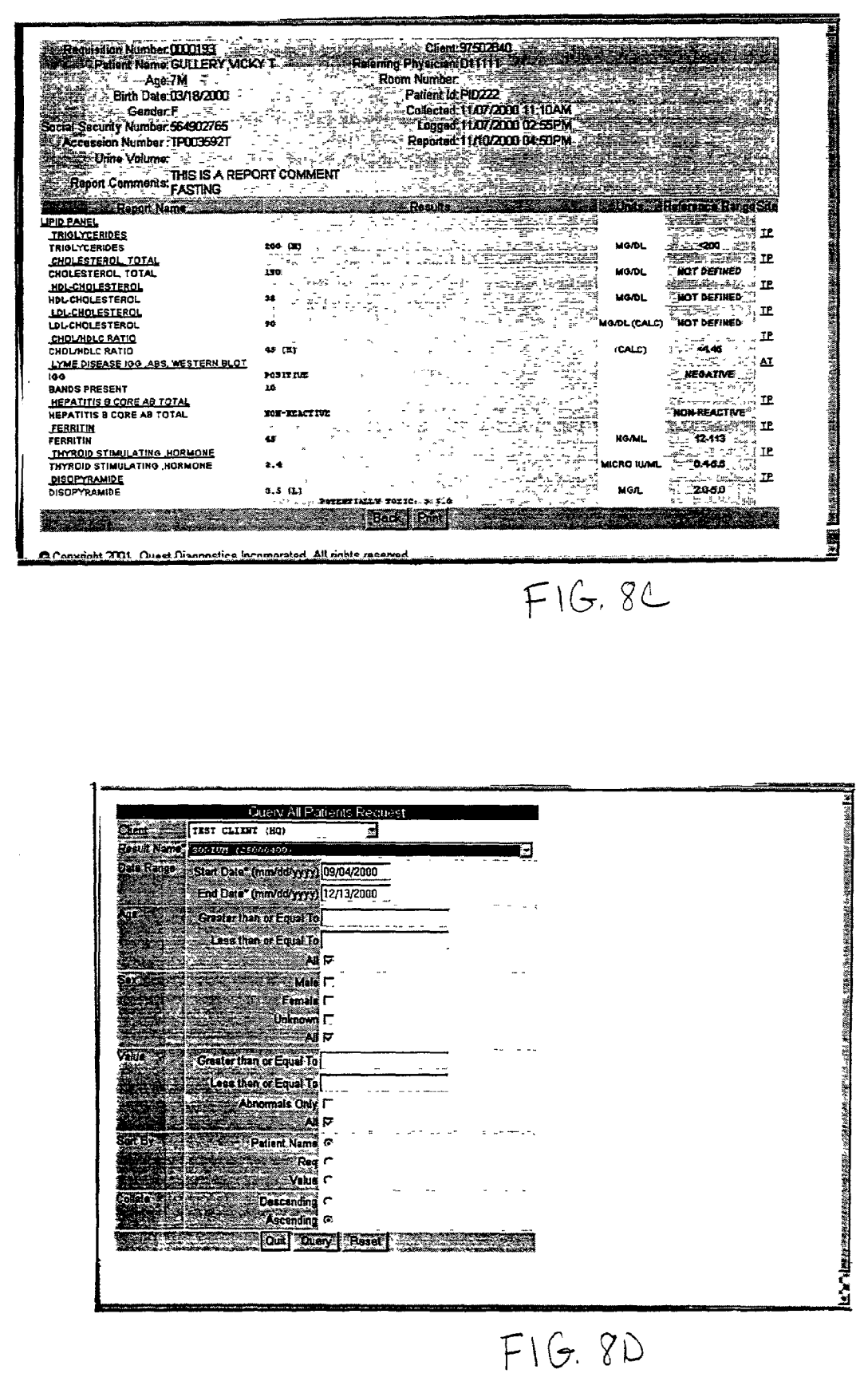

Assuming that step 126 is entered by selecting Patient Results, the client may select how results are to be printed or viewed (step 132). Examples of pages displayed on the screen for client prompting and an example of a printed report are shown in FIGS. 8A-8C. It will be appreciated that the report may be printed or viewed with all test results shown or only abnormal results shown. Partial test results or final test results may be selected for printing or viewing. Test results may be limited to selected start-to-end dates.

If the client selects Result Informatics, step 128 is entered and the query-all-patients-request page is displayed on the screen as shown, for example, in FIG. 8D. The client may select the criteria of the report (for example, all male patients who have taken a specific test, between a specified time period, and are in a specified age range). After the client selects a desired criteria, a query-results page is displayed in step 134, satisfying the selected criteria. An example of a query-results page is shown in FIG. 8E. The client may then select one report or several reports by clicking on a requisition number.

Finally, if the client selects Cumulative Reports, step 130 is entered. An example of a cumulative-report page is shown in FIG. 8F. The client may enter a patient's identity (for example, SSN) and a number for the number of reports to retrieve as historical data. For example, the last two reports for a patient may be retrieved. The reports are displayed in step 136 and may also be printed.

In this manner, the embodiments of the invention provides an interactive method for viewing or printing test results of a patient, based on client selected criteria. The criteria may be based on a desire to view test results of a particular patient; the test results may be for the most recent test conducted on that patient or test results for several previously conducted tests. The criteria may also be based on a desire to select a patient who fits a specific category (for example, a male, age 42 who ordered a blood test in the last two months). Thus, the exemplary method provides a flexible range of test report selection and presentation.

Figure 9I:
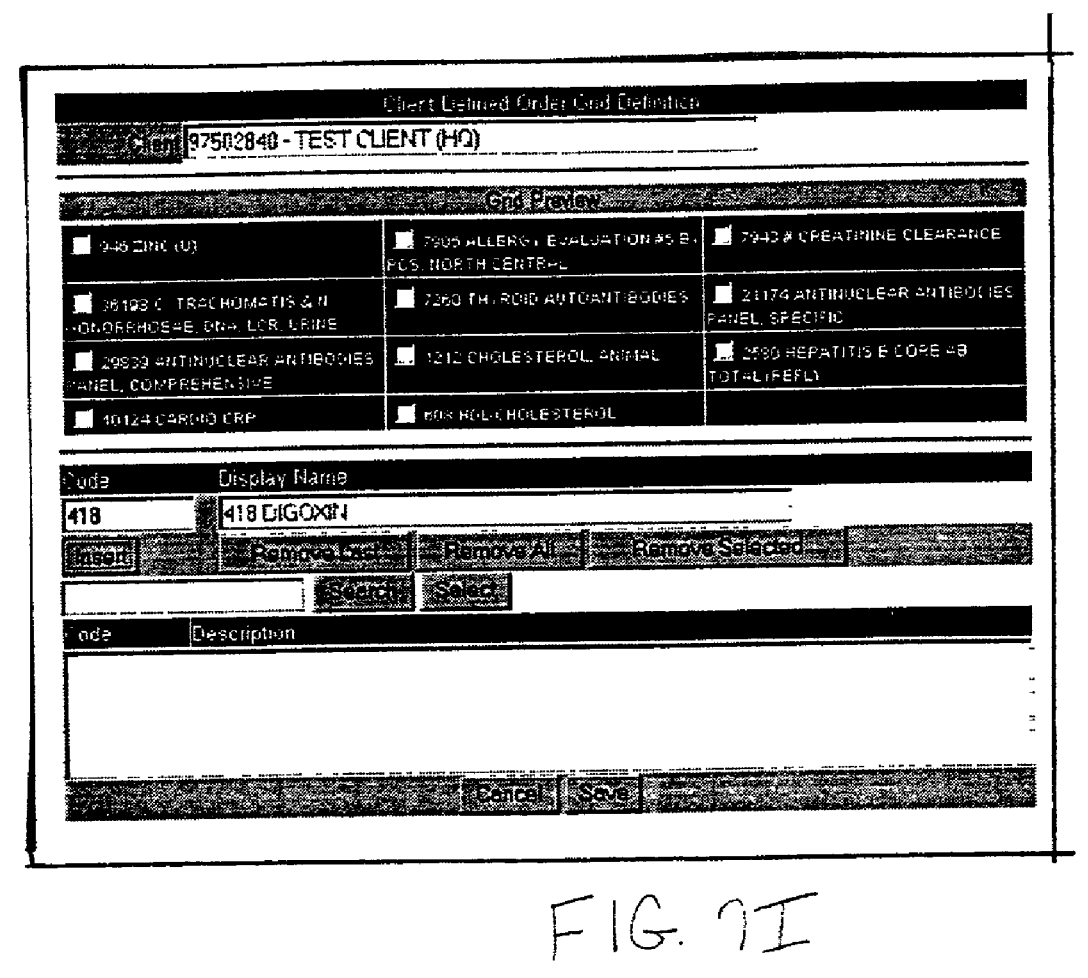
Figure 6:
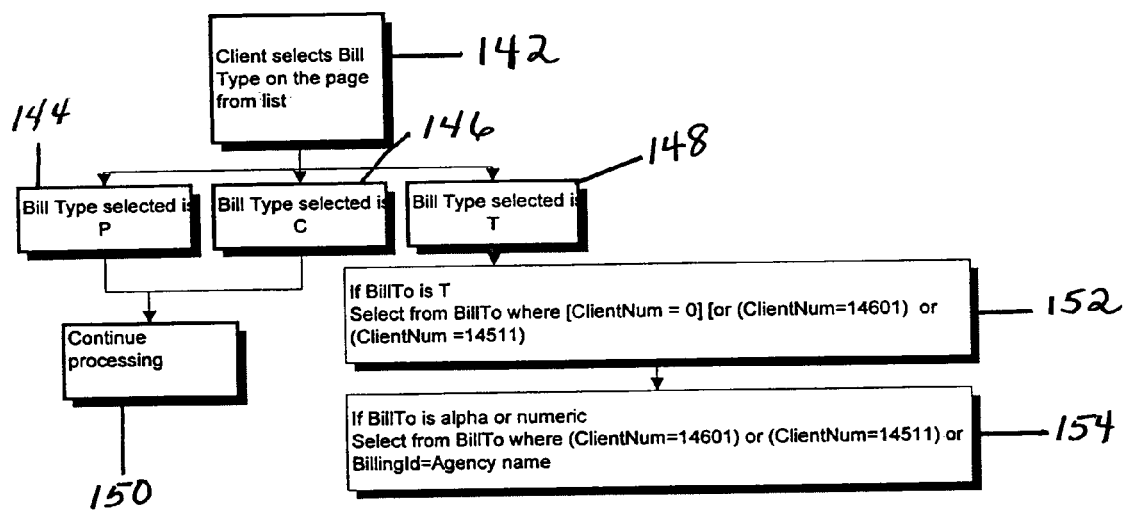
FIG. 6 is a flowchart diagram illustrating an embodiment of a method for providing billing information for a test ordered for a patient in the computer network of FIG. 1.
Figures 9A, 9B:
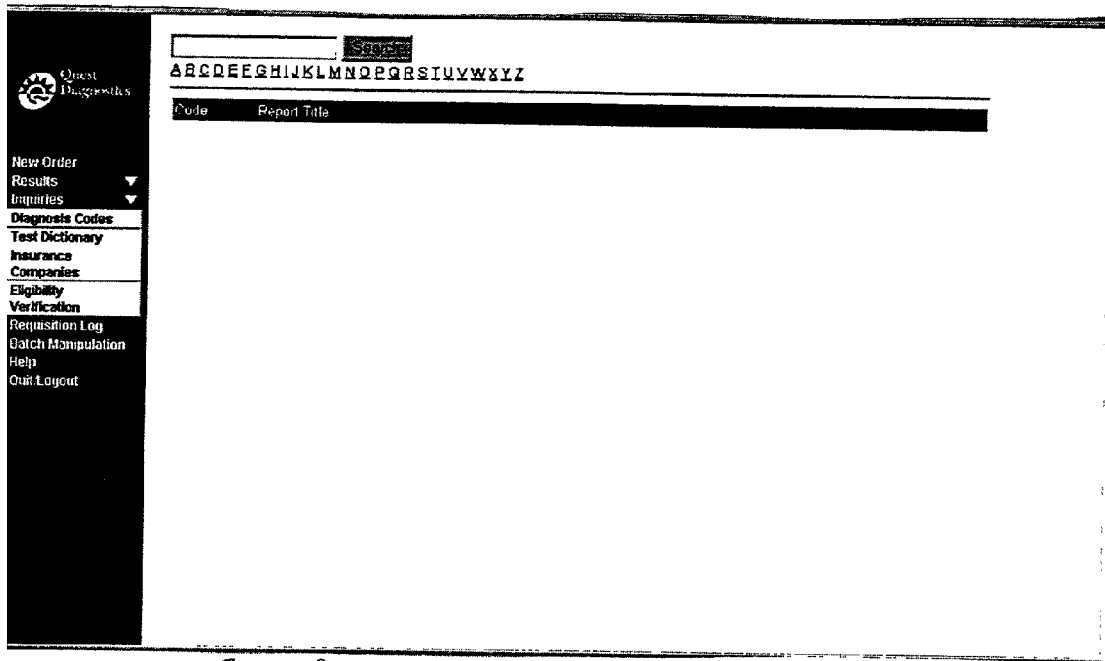
FIGS. 9A through 9B are embodiments of screen snapshots of various pages or documents provided by the method shown in FIG. 6 for entering billing information for a test ordered for a patient in the computer network of FIG. 1.

Referring to FIG. 6, an exemplary billing method 140 is depicted. The client may select in step 142 a billing type by entering patient information on a patient-information page, as shown in FIG. 7B, for example. The billing type entered may be (1) billing to the patient (P) (step 144), (2) billing to the client (C) (step 146), or (3) billing to a third party (T), for example, an insurance carrier (step 148). If the billing type is P or C, processing continues (step 150) as described in detail later. If the billing type is T then the client number is identified for billing (step 152) or any agency name (for example an insurer's name) may be identified for billing (step 154). An example of an insurance verification page provided to the client computer is shown in FIG. 9B. The client is requested to fill in the insurance company name and the member number that identifies the member covered by the insurance company and the relationship between the patient and the member. Automatic eligibility checking occurs behind the scenes and is transparent to the user. The eligibility is performed by the system on patient orders whose insurance carriers have valid eligibility master accounts (identified by the master mnemonic in the data file. Master mnemonic is an abbreviation that defines a particular carrier). When the system detects that an order is being placed for the carrier with a master mnemonic, it verifies the eligibility based on the insurance ID and patient information and displays the eligibility status on the order-verification page, such as verified, unknown, or unable to verify.

Having described exemplary methods which embody the invention, in general, the screen snapshots displayed during various steps of the methods will now be described in detail.

The member login screen may be the first screen the client sees after accessing a segment of the Web site, called the "New Order" segment, through the network to enter a new order. The exemplary member login screen of the "New Order" segment is shown in FIG. 7A. In order to access the system, the client enters a valid combination of User Name and Password. The system then enables the client to file an order. After entering valid login information, the client is presented with the next screen.

The next screen is the introductory screen. When the user clicks on New Order, the next screen in the exemplary system the patient-information screen, an example of which is shown in FIG. 7B. This screen is filled in by the client, when placing the order for a laboratory test, as follows:

1. In the Client field, select the client placing the order.
2. In the UPIN field, select the physician. Depending on the performing laboratory, there may be a Physician ID hyperlink in place of the UPIN.
3. To define any clients receiving additional result report copies, click Additional Report Copies.
4. A new patient may be added by entering the Patient's social security number in the SSN field and/or a patient ID in the Patient ID field. An existing patient may be retrieved in two ways:
   (a) by entering the patient's social security number and clicking Retrieve, or
   (b) by clicking Search; clicking either Name or Patient ID; entering a full or partial patient last name or ID in the box provided; adding DOB to the search by entering it in the DOB field and clicking Search; all patients meeting the criteria are displayed. After highlighting and clicking Select, the patient and patient information are displayed.
5. The fields for a new patient may be completed, if necessary, by editing the fields for an existing patient. All required fields are marked with an *. The zip code in the State or Zip field may be typed then [Tab] may be pressed. The city, state, and zip code fields are automatically populated.
6. Press Continue to move to the next screen.

An example of a billing information screen is shown in FIG. 7C. This screen includes responsible party and insurance information. The information displayed on this screen depends on entries on the patient-information screen. If "client" is selected, the billing information screen does not appear. If "patient" is selected, responsible party information appears, but not insurance information. If "insurance" is selected, both responsible party and insurance information appear.

The billing information screen is filled in by the client, as follows:

1. If displayed, the responsible party information is corrected, if necessary.
2. Insurance information is entered as follows:
   (a) Insurance Carrier or Generic Carrier: Go to the appropriate field and type the first letter of the insurance carrier or click the down arrow for a list of carriers. Select the correct carrier.
   (b) Insurance ID: Enter the insurance ID number.
   (c) Group Number: Enter the group number.
   (d) Referring Physician Provider ID: Enter the ID. For Medicare carriers this field may be populated automatically with a physician's name.

3. Click Continue.

The diagnosis-for-patient screen may be displayed next. An example of a diagnosis-for-patient screen is shown in FIG. 7D. To complete the diagnosis screen, the following steps are performed by the client:
1. In the Diagnosis field, either type the diagnosis code directly into the box OR search for a code.
2. Once a code is added, press <TAB> to move to the next box to add additional codes. After moving to the next box, the description of the previous code is displayed in the Description field.
3. If the client has defined a custom ICD grid, the box next to the ICD codes displayed in the shaded grid is clicked. To define or edit the ICD codes that appear in the grid, Edit ICD Grid is clicked.
4. Steps 1,2&3 are repeated until all the desired diagnosis codes have been added. Up to 10 codes may be entered.
5. To clear all the diagnosis codes and begin again, click Clear Codes.
6. Click Continue to move to the next screen.

The test-ordering-for-patient screen may be the next screen. An example of a test-ordering-for-patient screen is shown in FIG. 7E. If a regular insurance carrier is selected, then the following steps may be performed by the client to complete the test-ordering-for-patient screen:
1. The date the specimen was collected is entered in the Date Collected field. The date format is MM/DD/YYYY. To default to today's date, T is typed. To default to yesterday's date, Y is typed. T-# may also be entered. For example, T-14 is 14 days ago from today's date.
2. The time (HH:MM AM/PM) the specimen was collected is entered in the Time field. To default to the current time, N may be typed.
3. The amount collected in the Total Vol. Field is entered. A 2-4 digit number, an R for random, or NOTV for no total volume may also be entered.
4. The duration in the Duration field is entered (if applicable).
5. If the patient fasted, the Fasting field is clicked. If not, it is left blank.
6. There are different ways to enter the order codes.
   (a) The order codes may be typed directly in the Order Codes field.
   (b) If the user has defined a custom order grid (described later), the box next to the order codes displayed in the grid may be clicked. To define or edit the order codes that appear in the grid, Edit Custom Order Grid may be clicked.
   (c) A code or test name may be searched.
   (d) The Standing Orders link may be clicked. This hyperlink may be used if the patient has standing orders or the client wishes to define standing orders.
   (e) The Directory of Services link may be clicked to search for order codes using the Directory of Services.
7. Once a code is added <TAB> may be pressed to move to the next box in order to add additional codes.
8. Steps 6&7 may be repeated until all of the desired order codes have been added. Up to 15 codes may be entered.
9. To clear all of the order codes and begin again, Clear Codes may be clicked.
10. Upon clicking Continue, the next screen is displayed. The screen that is displayed next depends on the tests ordered.

An example of standing-orders-for-a-patient screen is shown in FIG. 7F. The client may define standing orders for a patient or edit existing standing orders by using this screen. The Standing Orders screen may be accessed through a hyperlink on the test-ordering-for-patient screen. The following steps may be performed to define or edit standing orders:
1. The code may be typed directly into the box or a code may be searched.
2. Once a code has been added, <TAB> is pressed to move to the next box to add additional codes.
3. Steps 1 and 2 may be repeated until all the desired codes have been added/edited/deleted. Up to 15 codes may be entered.
4. An optional expiration date may be entered for standing orders. When the standing orders expire, the order may be filed again on the standing orders screen.
5. When all the standing orders appear as desired, File Standing Orders may be clicked. The client is returned to the test-ordering-for-patient screen.

The client may view the directory of services by clicking on the hyperlink on the test-ordering-for-patient screen shown in FIG. 7E. The directory-of-services screen is shown in FIGS. 7G and 7H as examples. As shown, the preferred specimen for DIGOXIN is described. The specimen volume, container, transport temperature, and stability are also shown.

In one embodiment of the invention, the client may customize the tests appearing in the shaded grid on the test-ordering-for-patient screen (FIG. 7E). The client may define or edit the custom order grid by performing the following steps:
1. Edit Custom Order Grid is clicked from the test-ordering-for-patient screen.
2. The client-defined-order-grid-definition screen appears, as shown, for example, in FIG. 7I. The following tasks from this screen may be performed:
   (a) Add an order code: An order code is typed in the Code field and Insert is clicked. The new code is added to the grid.
   (b) Delete a code: A check mark is placed next to the code or codes to be removed and Remove Selected is clicked. To remove the last code entered, Remove Last is clicked.
   (c) Deleting all the codes in the grid may be done by clicking Remove All.
   (d) Searching for order codes may be done by entering a test code into the box next to the Search button field and clicking Search.
   (e) The client may precede and/or follow the search string with an asterisk * to expand search (e.g. 123*). Entering a partial search string (e.g. 42) returns results 34289, 6442, 423, for example.
   (f) Selecting multiple search results may be done by holding down the SHIFT key or the CTRL key, while highlighting selected records. Clicking Select adds multiple test order codes to the grid. Double clicking adds one record.
3. Clicking Save saves all the changes; clicking Cancel leaves without saving the changes. The same steps apply to editing the ICD Grid.

Figure 12:
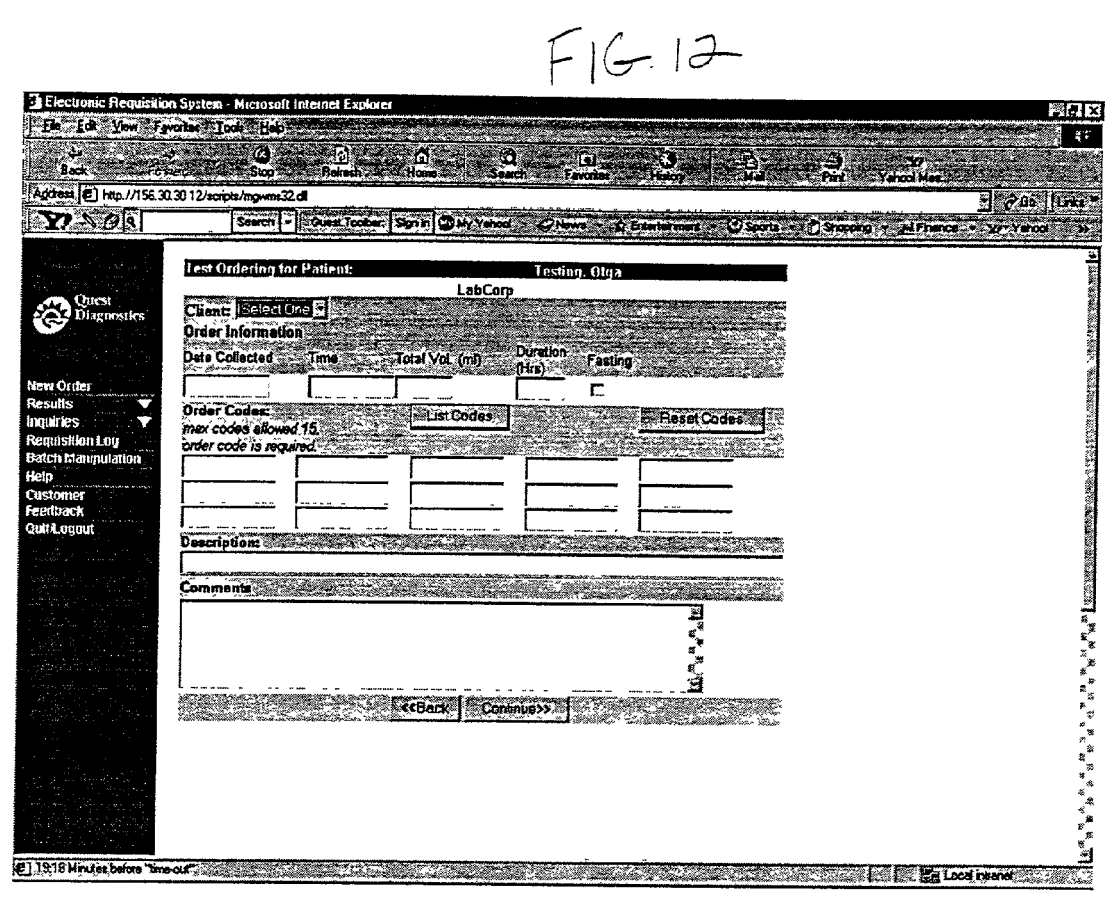

According to another aspect of the invention, a generic test-ordering screen such as the one illustrated in FIG. 12 may be provided. So-called "Generic Requisitions" can be used when a client wants to use the system to send orders to a different facility. A system administrator can define a Generic Requisition using the client's account number and a list of order codes for the different facility. The application then prints out the requisition for the client to send to the different facility.

To use the generic test-ordering screen shown in FIG. 12, the user selects the generic insurance carrier from the drop down list on the Billing Information screen (FIG. 7C), and the system checks which laboratory has been set up for this client for this insurance carrier. The diagnosis screen (FIG. 7D) can be displayed next, followed by the generic test-ordering screen. After the user enters the order codes, the order verification screen is displayed. After the order is submitted, the Generic Requisition can be printed. There need be no medical necessity or AOE (ask-at-order-entry) functionality for Generic Requisitions.

It will be appreciated that the invention provides benefits to the client. For example, the diagnosis-for-patient page and the test-ordering-for-patient page may be customized by the client. In this manner, codes most commonly used by a particular client for identifying diagnoses of its patients and tests ordered for its patients that are medically necessary for treatment of the patients may be presented on the client's computer screen every time the client computer communicates with the central computer. For example, a gynecologist is typically interested in a set of test orders for specific diagnoses of his or her patient that is different from the set of test orders and diagnoses made by an orthopedist or an internist for his or her patients. By customizing the codes for each client, the system is personalized, user friendly and flexible.

Some tests may require additional information before the laboratory can perform the ordered tests. The ask-at-order-entry (AOE) screen, shown for example in FIG. 7J, appears on the client computer, prompting the client to answer the questions. The information on this screen varies depending on what test(s) are ordered. This screen lists all AOE questions for every test ordered that has associated AOE questions. The screen is displayed after test(s) are ordered from the test-ordering-for-patient screen. When the client finishes answering the questions, Continue may be clicked. To return to the previous screen, Back may be clicked.

An example of the advance-beneficiary-notice screen (ABN) is shown in FIG. 7K. This screen is a reminder that limited coverage tests require specific diagnosis codes indicating medical necessity to justify reimbursement for the services. When an ICD code is entered that is not reimbursable by Medicare, for example, the client is prompted to have the Medicare beneficiary sign an ABN. Clicking Submit to continue brings up the order-verification-for-patient screen.

The order-verification-for-patient screen is shown in FIG. 7M. This screen includes all the information entered for a specific order. The client is prompted to review the information entered for correctness. If the information is correct, the client may click File Order.

If changes are to be made, the Edit Order button may be clicked. The client is then returned to the patient-information screen, from which continue may be clicked until the appropriate screen that is to be modified is displayed. The client may also click on a section heading hyperlink (e.g. Patient Information) to be returned to a specific screen. Clicking on the test order codes displays the directory-of-services screen for the test order code clicked.

When the client clicks File Order in the order-verification screen, the requisition screen, shown for example in FIG. 7N, is displayed. The client may print the requisition displayed on the screen. The client may also print the specimen labels for the requisition. An example of a specimen label printed by the client to be placed on a test order is shown in FIG. 7L.

The client may print result reports based on a flexible selection criteria. For example, the client may select Results and then Patient Results on the left menu bar shown in FIG. 8A. The report-print screen shown in FIG. 8A is displayed. The fields shown are then completed. When completed, Query is selected. The selected-reports screen is displayed, as shown, for example, in FIG. 8B. A list of selected reports is presented. Each report includes a requisition number, patient name, date, status (final, partial) and an abnormal flag, as shown. To print a selected report, the client may click Print to the right of the desired report.

The selected report appears on the screen, as shown, for example, in FIG. 8C. Clicking OK on the browser print box sends the report to the printer. A single report or multiple reports may be printed. In order to view the selected report, the client may click View to the right of the desired report. A view-only version of the report is displayed with hyperlinks to the directory of services. Clicking on New Query returns the client to the report-print screen, shown in FIG. 8A.

If the client selects Results and then Result Informatics on the left menu-bar shown in FIG. 8A, the query-all-patients-request screen shown in FIG. 8D may be displayed as an example. All shown fields may be completed and then Query may be selected. The query-results screen, as shown for example in FIG. 8E, is displayed. A list of selected reports is presented. A requisition number, date collected, patient name, DOB, age, sex and result flag may be included for each report. To print a selected report, the client may click a Requisition hyperlink. After clicking the hyperlink, the report appears on the screen. Clicking OK on the browser print box sends the report to the printer. If the client clicks New Query, the query-results screen is returned. Clicking Quit returns the client to the patient-information screen.

Cumulative reports may be viewed by clicking Results and selecting Cumulative Reports on the left menu-bar, shown in FIG. 8A. The cumulative-reporting screen appears, as shown, for example, in FIG. 8F. The cumulative report may require at least two distinct requisition numbers that match the provided SSN. The client may enter the patient's social security number in the SSN field. The number of reports to go back to may also be entered. After clicking Query, the report appears on the screen. Clicking OK on the browser print box sends the report to the printer.

In one embodiment of the invention, an inquiry option is provided. The purpose of inquiries is to perform a quick look up, without having to place an order. The inquiry option may be entered by clicking Inquiries on the left menu-bar shown in FIG. 9A. The following inquiry options may be available: diagnosis codes; test dictionary; insurance companies; and eligibility verification. The following are client specific result information: custom result queries by client, result, name, date range, sex, value, or a combination of all.

In order to verify a patient's eligibility for insurance; the client may perform the following steps:

1. From any screen in the system, click Inquiries, then Eligibility Verification located in the menu-bar on the left of the screen. The screen shown in FIG. 9B may be displayed as an example.
2. Select Insurance Company.
3. Enter information regarding the patient.
4. Enter date of service (may default to today's date).
5. Click Query. If a patient's eligibility cannot be verified, a message is displayed noting inability to verify eligibility.
6. Click Reset to perform another search or click Quit to close the window.

In another embodiment of the invention, a requisition log may be printed. The requisition log prints a log of all requisitions filed based on a given client and/or a range of dates. In order to print a log, the client may perform the following steps:

1. Click Requisition Log located on the left menu-bar of the screen shown in FIG. 8A, for example. The requisition-log-report-request screen shown in FIG. 10, for example, appears.
2. In the Client field, select one or more clients. To select multiple clients:

Press the [Shift] key and click the mouse to select a group of clients.

Press the [Ctrl] key and click the mouse to select individual clients.

3. In the Order Type field, click desired choice of laboratory:
   (a) Quest Only
   (b) Non-Quest Only
   (c) All
4. In the Date Type field, click desired choice:
   (a) Order Date—Date the order was placed.
   (b) Collection Date—Date the specimen was collected.
5. In the Date Range field, enter a start and end date for the report. Date formats are MM/DD/YYYY. To default to today's date type T. T-# may also be entered, for example, T-14 is 14 days ago from today's date.
6. In the Sort By field, click desired choice:

Date—Log is sorted starting with the earliest date.

Patient Name—Log is sorted by Patient's last name.

7. Click Query. The report appears on the screen. A client may also reprint a requisition by clicking on the corresponding req # link on the report.
8. To print the report click File, Print (the menu choice may depend on the browser) or the Print icon. If the browser print box comes up, click OK. To close without printing, click Close.

A requisition applet may be included to allow for splitting of requisitions based on test ordering. This may include specimen labels for each new requisition created.

A print applet may be included to allow the system direct access to a browser's printer. With the applet, the system may create barcodes and other printed material with exactness not possible in HTML. There may be two different versions of the applet contained in two separate files on the server. The Print class may evaluate at run time which browser the client is using and may change the applet tag dynamically to accommodate the browser.

The applet supports multiple pages and reprinting. The applet is typically device independent. It may draw to any laser or ink based printer capable of printing within Windows. The entire jar/cab file may be less than 10 k. This ensures a minimum download time to the client. The applet may communicate with the web server via SSL. The necessary printing commands may be passed as parameters to the java applet via the web page connected via SSL. In this manner, all communication may remain encrypted.

In yet another embodiment of the invention, the client may print a manifest report. The manifest report permits the client to view the orders for a specific batch of tests or test specimens that are forwarded together in a group. To print the report, the client may perform the following steps:

1. From any screen in the system, click Batch Manipulation located in the menu-bar on the left of the screen. The batch-processing screen shown, for example, in FIG. 11 appears.
2. In the Ordering Client field, select the client for whom the manifest is to be printed.
3. In the Open Batches field, select the batch to print. The batch status is displayed.
4. Click Print. The report displays on the screen.
5. To navigate through the report, the client may use the Next Page and Prev Page buttons.
6. Click Print to print the report.
7. Click Return to return to the batch processing Screen or click Quit to exit from Batch Processing.

The minimum recommendations for an exemplary embodiment of the system are given in Table 5.

TABLE 5

Recommendations for accessing the system

| | |
|---|---|
| Internet Connection: | Modem min speed 56.6 bps or direct connection |
| Browser: | Internet Explorer or Netscape version 4.0 or greater Security Encryption: 128 bit |
| Hardware: | Pentium 100 Mhz or greater, 32 MB RAM OR Macintosh with a PowerPC processor 8 MB of RAM with Virtual Memory on (12 MB recommended) 15 MB of hard disk space for Internet Explorer Apple MRJ 2.1 or above 800 × 600 video resolution Mouse Laser or Inkjet printer (no dot matrix) |
| Operating Systems: | Windows 95, 98, NT 4.0 or greater, MacOS 8.1, UNIX, LINUX |

The files may be used by the system and stored in database 34 are listed in Table 6. A description of each file is also provided in the table.

TABLE 6

Files and Description of files.

| File Name (.txt) | Table Name | Table Description |
|---|---|---|
| AOE | AOE | Contains the UNIT Code and its associated Analytes the analytes contain the Ask at order entry questions . . . , needed to process the test |
| BILL_TO | BILL_TO | Valid bill to's (clients and ins carriers from TopLab. |
| BILLCD | BILL_TO_ELIGIBILITY | Eligibility carriers |
| BILLEDIT | BILLING_EDITS | Billing edits contained in NBS |
| CLIENT | TOPLAB_CLIENT | TopLab client information |
| CLBTX | CLIENT_BIL_TO_XREF | Client Bill-to cross-reference |
| CPTICD9 | ISP_CPT_ICD_PAYABLE | Links CPT codes to diagnosis codes for a given dataset. |

TABLE 6-continued

Files and Description of files.

| File Name (.txt) | Table Name | Table Description |
|---|---|---|
| EDITLIST | BILLING_EDIT_LISTS | Billing edits containing the valid values required when editing certain third parties |
| ICD9_CD | No corresponding table-one time load from SCAN system for this version | List of diagnosis codes |
| ORDCODE | TEST_CODE_UNIT_CODE_XREF | Test code and its associated unit code |
| ORDERCPT | ORDERABLE_CPT | Links orderable test codes to CPT codes for a given dataset. |
| QUESTLAB | | Cross-reference-LIS/BIS Eligibility carriers to Eligibility system carriers for non-TOPLAB sites |
| SITE | None | Direct from LIS-Site Code disclosure information for report |
| UPIN | CLIENT_UPIN | Direct from LIS-Site code disclosure information for report cross reference of UPIN with client. Contains provider name. |
| PROFILE | PROFILE_COMPONENT_XREF | Profiles order codes with components |
| CONTAINER | CONTAINER | Directory of services information |
| CPTCODES | TEST_CODE_UNIT_CODE_XREF_BILLING_PROCEDURE_CODE | Directory of services information |
| HEMOLYSIS | SPECIMENT_REJECT_HEMOLYSIS | Directory of services information |
| LIPEMIA | SPECIMENT_REJECT_LIPEMIA | Directory of services information |
| METHODOLOGY | METHODOLOGY | Directory of services information |
| SPECIMENREQ | PREFERRED_SPECIMEN_REQUIREMENT | Directory of services information |
| SPECIMENSTAB | SPECIMEN_STABILITY | Directory of services information |
| SPECIMENVOL | MINIMUM_SPECIMEN_VOLUME | Directory of services information |
| THAWOTHER | SPECIMEN_REJECT_THAW_OTHER | Directory of services information |
| TRANSPORT | | Directory of services information |
| WEBIGNITE.OK | None | Empty file placed to indicate completion of download from OERDB |

The network system includes an encryption technique to ensure the security of information transmitted between the client computer and the central computer. The encryption can be, for example, 128 bit encryption provided by the Web browser software. In addition, each session includes a unique session identifier (for example, a multiple character, alphanumeric code) that is used to verify a valid session traversing through every Web page within the system.

The system also senses a "brute force" attack from another computer and deactivates login capability from that particular computer. The denial of service is based on 10 failed attempts in a 15-minute window from the same computer. The system automatically restores privileges and resets counters in 10 minutes.

The system may also provide as a graphic the amount of idle time available to the user. In this manner, inactivity by the user may be limited. This provides additional security.

An XML bridge may also be provided to a user's POS (physician office system). The XML Bridge allows the end user to communicate to existing office systems and extract data from the systems into Orders/Results On-Line. This bridge is browser independent. The bridge allows access to systems inside the user's firewall, i.e. the POS system does not need to be on or have access to the Internet. The operation of the bridge is transparent to the end user. The only requirement that the end user may have is entering an ID in querying the office management system. The system handles calls to multiple servers in the event that the end user wishes to query more than one system. The system handles up to 500 patients and allows the end user to browse and pick the appropriate patient. The system accepts returned data. Any missing data items may be filled in by the user in the regular ordering screens.

Other system features may be customized for the user either through a data feed or via an administration function. For example, bill to insurance carriers, billing edits, clients, UPINs, test dictionary, label printer or no label printer, result menu (no reports, reports only, reports/cumulative, reports/cumulative/result queries), etc., may be customized.

The system may also include a wireless results viewing capability by viewing results over an SSL link from a web enabled Palm® IIV, IIVx, or V. This capability allows the user to view medical results on patients on a 30, 60, or 90 day basis.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention. The invention is defined separately in the appended claims.

What is claimed is:

1. In a computer network including a client computer and a central computer, a method of receiving an order of a laboratory test of a biological specimen for a patient comprising the steps of:
   receiving, at the central computer, at least one query transmitted through the network from the client computer, the at least one query including a laboratory test request and patient, billing, and diagnosis information corresponding to the requested laboratory test;

transmitting information through the network from the central computer to the client computer, the information including data for generating a test requisition and a label for use with the biological specimen; and analyzing the at least one query at the central computer to verify that the requested laboratory test is payable by a responsible party identified in the billing information.

2. The method of claim 1, wherein said receiving step comprises receiving a diagnosis code and a laboratory test code as a part of the at least one query and said analyzing step comprises searching a code database for correspondence between the diagnosis code and the laboratory test code.

3. The method of claim 1, wherein said analyzing step comprises comparing an identified diagnosis and the requested laboratory test to a maximum value to determine whether a maximum number of tests has been exceeded for the identified diagnosis.

4. The method of claim 1, further comprising the step of transmitting a notification through the network from the central computer to the client computer if the requested laboratory test is not payable by the identified responsible party for an identified diagnosis.

5. The method of claim 4, further comprising the step of requesting an indication that the patient is responsible for payment in response to the notification.

6. The method of claim 1, further comprising the step of transmitting a request for additional diagnosis information through the network from the central computer to the client computer if the requested laboratory test is not payable by the identified responsible party for an identified diagnosis.

7. A computer readable medium including computer program instructions that cause a central computer, in a computer network including at least one client computer and the central computer, to perform a method of receiving an order of a laboratory test of a biological specimen for a patient, the method comprising the steps of:

receiving at least one query transmitted through the network from the client computer, the at least one query including a laboratory test request and patient, billing, and diagnosis information corresponding to the requested laboratory test;

transmitting information through the network to the at least one client computer, the information including data for generating a test requisition and a label for use with the biological specimen; and analyzing the at least one query to verify that the requested laboratory test is payable by a responsible party identified in the billing information.

8. The computer readable medium of claim 7, wherein the computer program instructions further cause the central computer to perform the step of transmitting a request for additional diagnosis information through the network to the client computer if the requested laboratory test is not payable by the identified responsible party for an identified diagnosis.

* * * * *